(12) United States Patent
Futami et al.

(10) Patent No.: US 10,548,990 B2
(45) Date of Patent: Feb. 4, 2020

(54) MODIFIED SIRNA AND PHARMACEUTICAL COMPOSITION

(71) Applicant: GeneCare Research Institute Co., Ltd., Kamakura-shi, Kanagawa (JP)

(72) Inventors: Kazunobu Futami, Fujisawa (JP); Yasuhiro Furuichi, Kamakura (JP); Satoshi Kaneto, Kamakura (JP)

(73) Assignee: GeneCare Research Institute Co., Ltd., Kamakura (JP)

( * ) Notice: Subject to any disclaimer, the term of this patent is extended or adjusted under 35 U.S.C. 154(b) by 0 days.

(21) Appl. No.: 15/749,191

(22) PCT Filed: Jul. 29, 2016

(86) PCT No.: PCT/JP2016/072261
§ 371 (c)(1),
(2) Date: Jan. 31, 2018

(87) PCT Pub. No.: WO2017/022650
PCT Pub. Date: Feb. 9, 2017

(65) Prior Publication Data
US 2018/0214574 A1 Aug. 2, 2018

(30) Foreign Application Priority Data
Jul. 31, 2015 (JP) .................................. 2015-151974

(51) Int. Cl.
C07H 21/04 (2006.01)
A61K 48/00 (2006.01)
C12N 15/113 (2010.01)
A61K 31/713 (2006.01)
A61P 35/00 (2006.01)

(52) U.S. Cl.
CPC ........ *A61K 48/0016* (2013.01); *A61K 31/713* (2013.01); *A61K 48/00* (2013.01); *A61P 35/00* (2018.01); *C12N 15/113* (2013.01)

(58) Field of Classification Search
None
See application file for complete search history.

(56) References Cited

U.S. PATENT DOCUMENTS

2007/0167384 A1* 7/2007 Leake ................... C12N 15/111
514/44 A
2009/0215867 A1 8/2009 Takagi et al.

FOREIGN PATENT DOCUMENTS

| EP | 1 625 853 A1 | 2/2006 |
|---|---|---|
| JP | 2007-525169 A | 9/2007 |
| JP | 2012-219085 A | 11/2012 |
| WO | 2004/100990 A1 | 11/2004 |
| WO | 2006/054625 A1 | 5/2006 |
| WO | 2009/127230 A1 | 10/2009 |
| WO | 2010/150159 A1 | 12/2010 |

OTHER PUBLICATIONS

Mohammed Amarzguioui et al., "Tolerance for mutations and chemical modifications in a siRNA," Nucleic Acids Research, vol. 31, No. 2, Jan. 15, 2003, pp. 589-595.
Dianne S. Schwarz et al., "Asymmetry in the Assembly of the RNAi Enzyme Complex," Cell, vol. 115, Oct. 17, 2003, pp. 199-208.
Anastasia Khvorova et al., "Functional siRNAs and miRNAs Exhibit Strand Bias," Cell, vol. 115, Oct. 17, 2003, pp. 209-216.
Kumiko Ui-Tei et al., "Guidelines for the selection of highly effective siRNA sequences for mammalian and chick RNA interference," Nucleic Acids Research, vol. 32, No. 3, Feb. 9, 2004, pp. 936-948.
Sorim Choung et al., "Chemical modification of siRNAs to improve serum stability without loss of efficacy," Biochemical and Biophysical Research Communications, vol. 342, Issue 3, Apr. 14, 2006, pp. 919-927 (Abstract only).
Kazunobu Futami et al., "Induction of mitotic cell death in cancer cells by small interference RNA suppressing the expression of RecQL1 helicase," Cancer Sci., vol. 99, No. 1, Jan. 2008, pp. 71-80.
Kazunobu Futami et al., "Anticancer activity of RecQL1 helicase siRNA in mouse xenograft models," Cancer Sci., vol. 99, No. 6, Jun. 2008, pp. 1227-1236.
Kazunobu Futami et al., "RecQL1 DNA repair helicase: A potential tumor marker and therapeutic target against hepatocellular carcinoma," International Journal of Molecular Medicine, vol. 25, 2010, pp. 537-545.
Kazunobu Futami et al., "Development of siRNA drug by RNAi technology," Pharmaceutical and Medical Device Regulatory Science, vol. 41, No. 1, 2010, pp. 19-26 (partial translation).
Akihito Arai et al., "RECQL1 and WRN Proteins are Potential Therapeutic Targets in Head and Neck Squamous Cell Carcinoma," Cancer Research, vol. 71, 2011, pp. 4598-4607.
Nicole T. Schirle et al., "The Crystal Structure of Human Argonaute2," Science, vol. 336, May 25, 2012, pp. 1037-1040.
Kazunobu Futami et al., "RECQL1 and WRN DNA repair helicases: potential therapeutic targets and proliferative markers against cancers," Frontiers in Genetics, vol. 5, Article 441, Jan. 9, 2015, pp. 1-11.

* cited by examiner

*Primary Examiner* — Kimberly Chong
(74) *Attorney, Agent, or Firm* — DLA Piper LLP (US)

(57) ABSTRACT

Double-stranded modified siRNA targeting a RecQL1 helicase gene includes a sense strand including the nucleotide sequence shown in SEQ ID NO: 1, and an antisense strand including the nucleotide sequence shown in SEQ ID NO: 2, wherein the sense strand includes 2'-substituted nucleotides at positions 2, 3, 4 and 13 in the nucleotide sequence shown in SEQ ID NO: 1, the sense strand further includes a 2'-substituted nucleotide(s) at one or more positions selected from the group consisting of positions 12, 14, 17, 18 and 19 in the nucleotide sequence shown in SEQ ID NO: 1, wherein the position 2' of the 2'-substituted nucleotides is —$R^1$, —$OR^1$, —$R^2OR^1$, —$OR^2OR^1$ or —$R^3OR^2OR^1$, wherein $R^1$ represents a $C_{1-4}$ alkyl group, and $R^2$ and $R^3$ independently represent a $C_{1-3}$ alkylene group.

11 Claims, 14 Drawing Sheets
Specification includes a Sequence Listing.

Fig. 1A Unmodified
```
                        2 3 4       8 9  11121314    171819
            5'-GUUCAGACCACUUCAGCUUTT-3'        SEQ ID NO:3
            3'-TTCAAGUCUGGUGAAGUCGAA-5'        SEQ ID NO:4
             19      151413   10      5 4
```

Fig. 1B QL-9
```
               •••        ••   ••••      •••
            5'-GuucAGAccAcuucAGcuuTT-3'        SEQ ID NO:5
            3'-TTCAAGUCUGGUGAAGUCGAA-5'        SEQ ID NO:4
```

Fig. 1C QL-15
```
               •••           ••••      •••
            5'-GuucAGACCAcuucAGcuuTT-3'        SEQ ID NO:24
            3'-TTCAAGUCUGGUGAAGUCGAA-5'        SEQ ID NO:4
```

Fig. 1D QL-16
```
               •••        ••  ••••
            5'-GuucAGAccAcuucAGCUUTT-3'        SEQ ID NO:7
            3'-TTCAAGUCUGGUGAAGUCGAA-5'        SEQ ID NO:4
```

Fig. 1E QL-17
```
               •••             ••••
            5'-GuucAGACCAcuucAGCUUTT-3'        SEQ ID NO:8
            3'-TTCAAGUCUGGUGAAGUCGAA-5'        SEQ ID NO:4
```

Fig. 1F QL-18
```
               •••           •••       •••
            5'-GuucAGACCACuucAGcuuTT-3'        SEQ ID NO:6
            3'-TTcAAGuCuGGUGAAGuCGAA-5'        SEQ ID NO:9
                 •   •   •           •
```

Fig. 1G QL-19
```
               •••           •••       •••
            5'-GuucAGACCACuucAGcuuTT-3'        SEQ ID NO:6
            3'-TTcAAGuCuGGUGAAGUCGAA-5'        SEQ ID NO:10
                 •   •   •
```

Fig. 1H QL-20
```
               •••           •••       •••
            5'-GuucAGACCACuucAGcuuTT-3'        SEQ ID NO:6
            3'-TTCAAGuCuGGUGAAGuCGAA-5'        SEQ ID NO:11
                     •   •           •
```

Fig. 1i QL-21
```
               •••           •         •••
            5'-GuucAGACCACUuCAGcuuTT-3'        SEQ ID NO:12
            3'-TTcAAGuCuGGUGAAGUCGAA-5'        SEQ ID NO:10
                 •   •   •
```

Fig. 1J QL-24
```
               •••           •
            5'-GuucAGACCACUuCAGCUUTT-3'        SEQ ID NO:23
            3'-TTCAAGUCUGGUGAAGUCGAA-5'        SEQ ID NO:4
```

Fig. 14A

```
              2 3 4      8 9  11121314    171819
Unmodified 5'-GUUCAGACCACUUCAGCUUTT-3'   SEQ ID NO:3
           3'-TTCAAGUCUGGUGAAGUCGAA-5'   SEQ ID NO:4
              19    151413  10      5 4
```

Fig. 14B

```
QL-2S  5'-GUUcAGACcACuUcAGCuUTT-3'   SEQ ID NO:13
       3'-TTcAAGucuGGuGAAGucGAA-5'   SEQ ID NO:14
```

Fig. 14C

```
QL-3S  5'-GUUcAGACcACuUcAGCUUTT-3'   SEQ ID NO:15
       3'-TTcAAGucuGGuGAAGucGAA-5'   SEQ ID NO:14
```

Fig. 14D

```
QL-5   5'-GUUcAGACCACuUcAGCUUTT-3'   SEQ ID NO:16
       3'-TTcAAGucuGGuGAAGucGAA-5'   SEQ ID NO:14
```

MODIFIED SIRNA AND PHARMACEUTICAL COMPOSITION

TECHNICAL FIELD

This disclosure relates to: modified siRNA inhibiting the expression of a RecQL1 helicase gene; an agent inhibiting RecQL1 gene expression and an agent that induces cell death, each comprising the modified siRNA; and a pharmaceutical composition that treats cancer comprising the modified siRNA.

BACKGROUND

DNA helicase is an enzyme that unwinds double-stranded DNA to a single strand, and plays an important role in various processes associated with genetic information such as DNA replication, repair, transcription, translation and recombination. There are a variety of types of DNA helicases. DNA helicase showing homology with the RecQ helicase of *Escherichia coli* is referred to as "RecQ type helicase."

Human genome includes 5 types of RecQ type helicases (RecQL1, WRN, RTS, BLM and RecQ5). Among these, mutations in the WRN, RTS and BLM genes cause genome instability diseases, namely Werner's syndrome, Rothmund-Thomson syndrome and Bloom's syndrome, respectively. On the other hand, involvement of RecQL1 and RecQ5 in diseases has not been reported.

RecQL1 helicase (also referred to as RecQ1 or RecQL) is considered to unwind the higher-order structure of DNA frequently seen during DNA replication, which is referred to as a holiday structure, and to promote DNA replication. In addition, RecQL1 is considered to form a complex with an MSH2/6 protein associated with mismatch repair, and to carry out the mismatch repair during genome replication. Moreover, it is known that RecQL1 is highly expressed in cancer cells and actively proliferating cells, but that the expression level thereof is low in cells at resting phase. The outline thereof is described in Futami et al. (2010), Pharmaceutical and Medical Device Regulatory Science PMDRS, 41(1): 19-26.

We earlier reported that mitotic catastrophe and mitotic cell death are induced to various cancer cells by a reduction in the expression level of RecQL1 helicase due to siRNA (WO 2004/100990, WO 2006/054625, JP Patent Publication No. 2012-219085 A, K. Futami et al. (2008), Cancer Sci., 99(1): 71-80, K. Futami et al. (2008), Cancer Sci., 99(6): 1227-1236 and K. Futami et al. (2010), Int. J. Mol. Med., 25: 537-545). It is believed that this is caused by the phenomenon that DNA damage generated as a result of DNA replication cannot repaired due to a reduction in RecQL1 helicase, and thereby the damaged cells directly proceed to the division cycle. We also reported that such siRNA that acts on RecQL1 shows antitumor activity in cancer-bearing model animals (WO '990, K. Futami et al. (2008), Cancer Sci., 99(6): 1227-1236 and K. Futami et al. (2010), Int. J. Mol. Med., 25: 537-545).

A method of inhibiting gene expression by siRNA is a widely applied research method. Since siRNA can be designed to target a specific sequence, it has high specificity and, thus, application of siRNA to pharmaceutical agents will be expected. However, since RNA is easily degraded by nuclease, it is problematic in that it is difficult for the RNA to exhibit a desired function when it is administered as a pharmaceutical agent to a living body. To overcome such a problem, it has been attempted to artificially chemically-modify a polynucleotide chain that constitutes siRNA by methylation, fluorination and the like to enhance the stability of the siRNA. However, it is known that the RNAi activity of siRNA is generally reduced by such modification.

It could therefore be helpful to provide: modified siRNA inhibiting the expression of a RecQL1 helicase gene; an agent inhibiting RecQL1 gene expression and an agent that induces cell death, each comprising the modified siRNA; and a pharmaceutical composition that treats cancer comprising the modified siRNA.

SUMMARY

We unexpectedly found that, when 2'-substitution such as 2'-methoxylation (2'-O-methylation) is introduced into nucleotides at specific positions in a sense strand, or in both a sense strand and an antisense strand, which constitute siRNA targeting a RecQL1 helicase gene, RNAi activity is enhanced. Taking into consideration the fact that the RNAi activity of modified siRNA is generally lower than that of unmodified siRNA, the aforementioned findings are extremely surprising.

We thus provide:

[1] Double-stranded modified siRNA targeting a RecQL1 helicase gene, comprising
a sense strand comprising the nucleotide sequence shown in SEQ ID NO: 1, and
an antisense strand comprising the nucleotide sequence shown in SEQ ID NO: 2, wherein
the sense strand comprises 2'-substituted nucleotides at positions 2, 3, 4 and 13 in the nucleotide sequence shown in SEQ ID NO: 1,
the sense strand further comprises a 2'-substituted nucleotide(s) at one or more positions selected from the group consisting of positions 12, 14, 17, 18 and 19 in the nucleotide sequence shown in SEQ ID NO: 1, and
the position 2' of the 2'-substituted nucleotides is —$R^1$, —$OR^1$, —$R^2OR^1$, —$OR^2OR^1$ or —$R^3OR^2OR^1$, wherein $R^1$ represents a $C_{1-4}$ alkyl group, and $R^2$ and $R^3$ independently represent a $C_{1-3}$ alkylene group.

[2] The modified siRNA according to the above [1], which has a higher cell death-inducing activity than unmodified siRNA having the same nucleotide sequence.

[3] The modified siRNA according to the above [1] or [2], wherein the sense strand further comprises a 2'-substituted nucleotide at position 11 in the nucleotide sequence shown in SEQ ID NO: 1.

[4] The modified siRNA according to any one of the above [1] to [3], wherein the sense strand comprises the 2'-substituted nucleotides at the following positions in the nucleotide sequence shown in SEQ ID NO: 1:
(a) positions 2, 3, 4, 11, 12, 13, 14, 17, 18 and 19,
(b) positions 2, 3, 4, 11, 12, 13 and 14,
(c) positions 2, 3, 4, 12, 13, 14, 17, 18 and 19,
(d) positions 2, 3, 4, 13, 17, 18 and 19,
(e) positions 2, 3, 4, 11, 12, 13, 14 and 17,
(f) positions 2, 3, 4, 11, 12, 13, 14 and 18,
(g) positions 2, 3, 4, 11, 12, 13, 14 and 19,
(h) positions 2, 3, 4, 11, 12, 13, 14, 17 and 18,
(i) positions 2, 3, 4, 11, 12, 13, 14, 17 and 19,
(j) positions 2, 3, 4, 11, 12, 13, 14, 18 and 19,
(k) positions 2, 3, 4, 12, 13, 17, 18 and 19, or
(l) positions 2, 3, 4, 13, 14, 17, 18 and 19.

[5] The modified siRNA according to any one of the above [1] to [4], wherein the antisense strand is not modified.

[6] The modified siRNA according to any one of the above [1] to [4], wherein the antisense strand comprises the 2'-substituted nucleotide(s) at one or more positions selected from the group consisting of the positions 5, 13, 15 and 19 in the nucleotide sequence shown in SEQ ID NO: 2.

[7] The modified siRNA according to the above [6], wherein the antisense strand comprises the 2'-substituted nucleotides at the following positions in the nucleotide sequence shown in SEQ ID NO: 2:
(i) positions 13, 15 and 19,
(ii) positions 5, 13, 15 and 19, or
(iii) positions 5, 13, and 15.

[8] The modified siRNA according to any one of the above [1] to [7], wherein the 2'-substituted nucleotide is a 2'-methoxy nucleotide or a 2'-aminomethoxy nucleotide.

[9] The modified siRNA according to any one of the above [1] to [8], comprising a 3'-overhang consisting of TT or UU.

[10] The modified siRNA according to any one of the above [1] to [9], wherein the sense strand and the antisense strand each are 19 to 25 nucleotides in length.

[11] The modified siRNA according to the above [9] or [10], wherein the nucleotide sequence of the sense strand consists of the nucleotide sequence shown in SEQ ID NO: 3, and the nucleotide sequence of the antisense strand consists of the nucleotide sequence shown in SEQ ID NO: 4.

[12] The modified siRNA according to any one of the above [1] to [11], wherein the sense strand has cholesterol bound at the 5'-terminus thereof.

[13] An agent inhibiting RecQL1 gene expression, comprising the modified siRNA according to any one of the above [1] to [12].

[14] An agent that induces cell death, comprising the modified siRNA according to any one of the above [1] to [12].

[15] A pharmaceutical composition that treats cancer, comprising the modified siRNA according to any one of the above [1] to [12].

[16] The pharmaceutical composition according to the above [15], wherein the cancer is ovarian cancer, breast cancer, melanoma, liver cancer, colorectal cancer, lung cancer, or cervical cancer.

This description includes part or all of the contents as disclosed in Japanese Patent Application No. 2015-151974, which is a priority document of this application.

We thus provide: modified siRNA inhibiting the expression of a RecQL1 helicase gene; an agent inhibiting RecQL1 gene expression and an agent that induces cell death, each comprising the modified siRNA; and a pharmaceutical composition that treats cancer comprising the modified siRNA.

BRIEF DESCRIPTION OF THE DRAWINGS

FIGS. 1A-1J are views showing the sequences of siRNAs used in experiments and the positions of 2'-methoxy nucleotides in the sequences. (a) shows unmodified RecQL1-siRNA, and (b) to (j) each show modified RecQL1-siRNA ((b) QL-9, (c) QL-15, (d) QL-16, (e) QL-17, (f) QL-18, (g) QL-19, (h) QL-20, (i) QL-21 and (j) QL-24, respectively). The upper strand of each siRNA is a sense strand, and the lower strand thereof is an antisense strand. The position of the 2'-methoxy nucleotide is indicated with a filled circle, an underline, and a small, boldface letter. In (a), the positions of C and U are indicated with numbers.

FIGS. 14A-14D are views showing the sequences of siRNAs used in comparative examples and the positions of 2'-methoxy nucleotides in the sequences. (a) shows unmodified RecQL1-siRNA, and (b) to (d) each show modified RecQL1-siRNA ((b) QL-2S, (c) QL-3S and (d) QL-5, respectively). The upper strand of each siRNA is a sense strand, and the lower strand thereof is an antisense strand. The position of the 2'-methoxy nucleotide is indicated with a filled circle, an underline, and a small, boldface letter. In (a), the positions of C and U are indicated with numbers.

DETAILED DESCRIPTION

Figure 2:
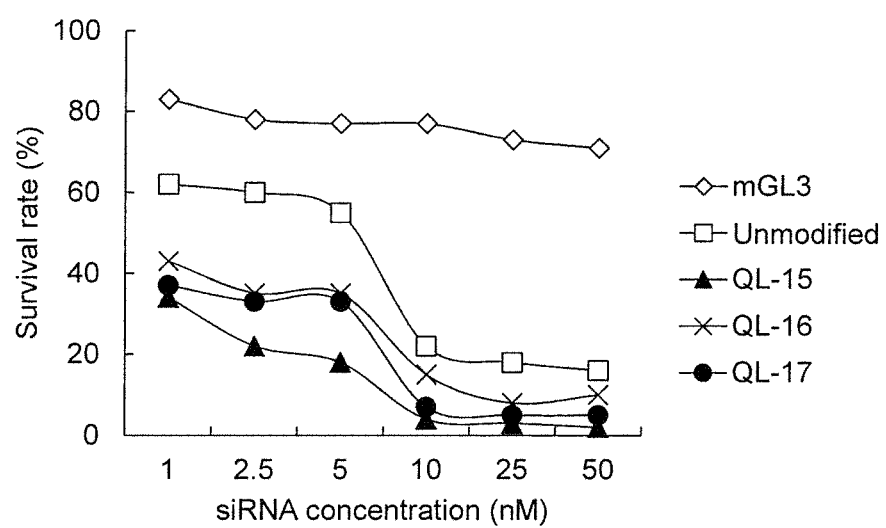
FIG. 2 is a graph showing the cell death-inducing activity of modified RecQL1-siRNAs (QL-15, QL-16 and QL-17) to ES-2 (ovarian cancer clear cell adenocarcinoma) cells.
Figure 3A:
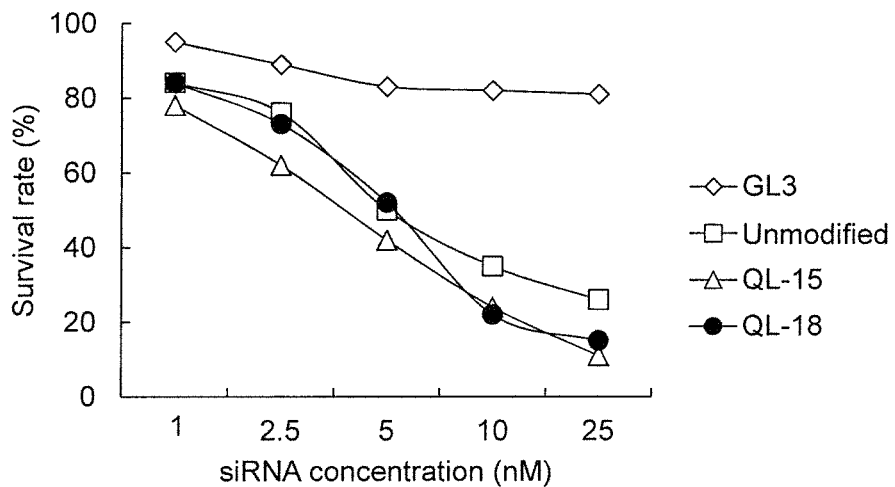
FIGS. 3A and 3B are graphs showing the cell death-inducing activity of modified RecQL1-siRNA (QL-18). The activity to (A) TOV-112D (ovarian cancer endometrioid adenocarcinoma) and (B) ES-2 (ovarian cancer clear cell adenocarcinoma) cells is shown.
Figure 3B:
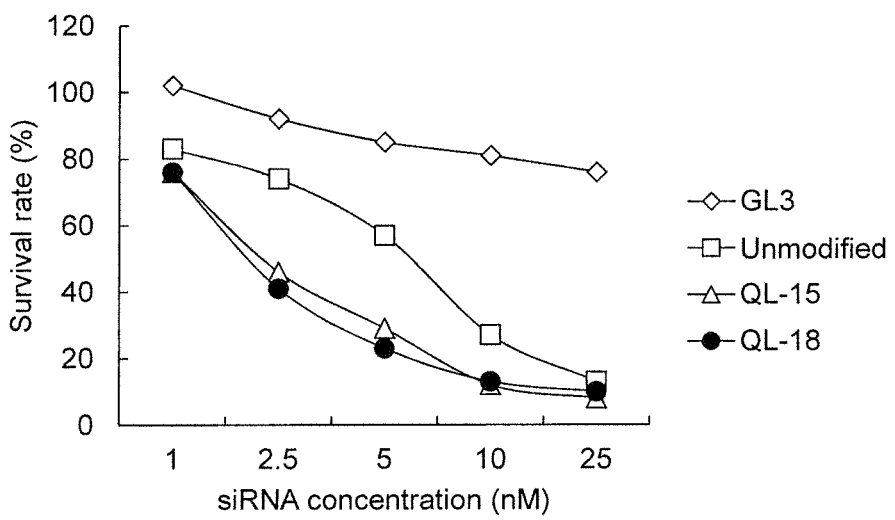

Hereinafter, our modified siRNA and pharmaceutical compositions will be described in detail.

Modified siRNA

We provide relates to double-stranded modified siRNA, which targets a RecQL1 helicase gene.

"siRNA" (short-interfering RNA) means double-stranded RNA having approximately 19 to 25 base pairs, which is capable of inducing inhibition of the expression of a target gene via RNAi. Such siRNA is composed of two polynucleotide chains, namely, the after-mentioned sense strand and antisense strand. The siRNA may also comprise a single-stranded portion (overhang).

"RNAi" (RNA interference) means a phenomenon by which the expression of a target gene is specifically inhibited in cells, into which double-stranded RNA having a sequence complementary to the sequence of the target gene (e.g., siRNA) has been introduced. The RNAi mechanism involving siRNA is typically as described below. First, one strand of siRNA introduced into cells is incorporated into a complex called "RISC (RNA-induced Silencing Complex)," and recognizes the mRNA of a target gene having a highly complementary sequence. The mRNA of the target gene is cleaved at the central portion of siRNA by RISC. Thereafter, the cleaved mRNA is degraded. Based on such a mechanism, siRNA can induce inhibition of the expression of a target gene via RNAi.

The siRNA targets a sequence comprising the nucleotide sequence 5'-GTTCAGACCACTTCAGCTT-3' (SEQ ID NO: 20) consisting of 19 nucleotides at positions 273 to 291 of a human RecQL1 gene coding region (SEQ ID NO: 19). The nucleotide sequence of human RecQL1 mRNA can be acquired from Genbank Accession No.: NM_002907.3 GI: 209977006.

The siRNA comprises:

a sense strand comprising the nucleotide sequence (base sequence) shown in SEQ ID NO: 1, and an antisense strand comprising the nucleotide sequence (base sequence) shown in SEQ ID NO: 2. The term "base" is used to mean a heterocyclic portion capable of pairing with the base of another nucleic acid. The nucleotide sequence shown in SEQ ID NO: 2 is a sequence complementary to the above-described nucleotide sequence (SEQ ID NO: 20) at positions 273 to 291 of a human RecQL1 gene coding region. The nucleotide sequence shown in SEQ ID NO: 1 is a sequence complementary to the nucleotide sequence shown in SEQ ID NO: 2.

The term "antisense strand" is used to mean a polynucleotide chain having a sequence complementary to the mRNA of a target gene. The term "sense strand" is used to mean a polynucleotide chain having a sequence complementary to the antisense strand (namely, having a sequence homologous to the mRNA of the target gene). The antisense strand is annealed to the sense strand to generate siRNA. The antisense strand binds to the mRNA of a target gene so that it can induce RNAi. The antisense strand constituting siRNA binds to the positions 273 to 291 of the coding region of RecQL1 mRNA so that it can induce RNAi. Thus, our siRNA can induce inhibition of the expression of a RecQL1 gene.

Our siRNA is modified. Preferably, the siRNA comprises a 2'-substituted nucleotide(s), more specifically, 2'-substituted pyrimidine nucleotide(s) (i.e., 2'-substituted uridylic acid (U) or 2'-substituted cytidylic acid (C)), at a specific position(s) of a sense strand, or of both a sense strand and an antisense strand. In particular, the sense strand constituting the siRNA comprises 2'-substituted nucleotides (2'-substituted pyrimidine nucleotides) at positions 2, 3, 4 and 13 in the nucleotide sequence shown in SEQ ID NO: 1. The position of a nucleotide shown is a position counted from the 5'-terminal side of a polynucleotide chain. The purine nucleotides of the sense strand (i.e., adenylic acid (A) and guanylic acid (G) at positions 1, 5 to 7, 10, 15 and 16) may be unmodified (natural type) nucleotides.

The sense strand constituting the siRNA further comprises a 2'-substituted nucleotide(s) at other positions, in addition to the positions 2, 3, 4 and 13 in the nucleotide sequence shown in SEQ ID NO: 1. Specifically, the sense strand further comprises a 2'-substituted nucleotide(s) (2'-substituted pyrimidine nucleotide(s)) at one or more, two or more, three or more, four or more, or all of five positions selected from the group consisting of positions 12, 14, 17, 18 and 19 in the nucleotide sequence shown in SEQ ID NO: 1. The sense strand may further comprise a 2'-substituted nucleotide at position 11 in the nucleotide sequence shown in SEQ ID NO: 1. The sense strand comprises unmodified (natural type) pyrimidine nucleotides at positions 8 and 9 in the nucleotide sequence shown in SEQ ID NO: 1.

In a specific example, the sense strand constituting the siRNA can comprise 2'-substituted nucleotides (2'-substituted pyrimidine nucleotides) at the following positions in the nucleotide sequence shown in SEQ ID NO: 1:
(a) positions 2, 3, 4, 11, 12, 13, 14, 17, 18 and 19,
(b) positions 2, 3, 4, 11, 12, 13 and 14,
(c) positions 2, 3, 4, 12, 13, 14, 17, 18 and 19, or
(d) positions 2, 3, 4, 13, 17, 18 and 19.

In this case, the sense strand may have unmodified (natural type) nucleotide(s) at position(s) other than the positions described in any one of the above (a) to (d), in the nucleotide sequence shown in SEQ ID NO: 1.

The sense strand can also comprise 2'-substituted nucleotides (2'-substituted pyrimidine nucleotides) at the following positions in the nucleotide sequence shown in SEQ ID NO: 1:
(e) positions 2, 3, 4, 11, 12, 13, 14 and 17,
(f) positions 2, 3, 4, 11, 12, 13, 14 and 18,
(g) positions 2, 3, 4, 11, 12, 13, 14 and 19,
(h) positions 2, 3, 4, 11, 12, 13, 14, 17 and 18,
(i) positions 2, 3, 4, 11, 12, 13, 14, 17 and 19,
(j) positions 2, 3, 4, 11, 12, 13, 14, 18 and 19,
(k) positions 2, 3, 4, 12, 13, 17, 18 and 19, or
(l) positions 2, 3, 4, 13, 14, 17, 18 and 19.

In this case, the sense strand may have unmodified (natural type) nucleotide(s) at position(s) other than the positions described in any one of the above (e) to (l), in the nucleotide sequence shown in SEQ ID NO: 1.

On the other hand, the antisense strand constituting the siRNA may be or may not be modified.

In an example in which the antisense strand is modified, the antisense strand may comprise a 2'-substituted nucleotide(s) (2'-substituted pyrimidine nucleotide(s)) at one or more, two or more, three or more, or four or more positions selected from the group consisting of positions 4, 5, 10, 13, 14, 15 and 19 in the nucleotide sequence shown in SEQ ID NO: 2. The purine nucleotides of the antisense strand (i.e., adenylic acid (A) and guanylic acid (G) at positions 1 to 3, 6 to 9, 11, 12, and 16 to 18) may be unmodified (natural type) nucleotides.

Preferably, the antisense strand may comprise a 2'-substituted nucleotide(s) (2'-substituted pyrimidine nucleotide(s)) at one or more, two or more, or three or more positions selected from the group consisting of positions 5, 13, 15 and 19 in the nucleotide sequence shown in SEQ ID NO: 2. In this case, the antisense strand may have unmodified (natural type) nucleotide(s) at position(s) other than the above-described positions (positions 5, 13, 15 and 19), in the nucleotide sequence shown in SEQ ID NO: 2.

In a specific example, the antisense strand can comprise 2'-substituted nucleotides (2'-substituted pyrimidine nucleotides) at the following positions in the nucleotide sequence shown in SEQ ID NO: 2:
(i) positions 13, 15 and 19,
(ii) positions 5, 13, 15 and 19, or
(iii) positions 5, 13, and 15.

In this case, the antisense strand can have unmodified (natural type) nucleotide(s) at position(s) other than the positions described in any one of the above (i) to (iii), in the nucleotide sequence shown in SEQ ID NO: 2.

Preferably, the sense strand may comprise 2'-substituted nucleotides at positions 2, 3, 4, 11, 12, 13, 14, 17, 18 and 19 in the nucleotide sequence shown in SEQ ID NO: 1, and the antisense strand may not be modified. Also preferably, the sense strand may comprise 2'-substituted nucleotides at positions 2, 3, 4, 11, 12, 13 and 14 in the nucleotide sequence shown in SEQ ID NO: 1, and the antisense strand may not be modified. Further preferably, the sense strand may comprise 2'-substituted nucleotides at positions 2, 3, 4, 12, 13, 14, 17, 18 and 19 in the nucleotide sequence shown in SEQ ID NO: 1, and the antisense strand may comprise 2'-substituted nucleotides at positions 5, 13, 15 and 19 in the nucleotide sequence shown in SEQ ID NO: 2. Still further preferably, the sense strand may comprise 2'-substituted nucleotides at positions 2, 3, 4, 12, 13, 14, 17, 18 and 19 in the nucleotide sequence shown in SEQ ID NO: 1, and the antisense strand may comprise 2'-substituted nucleotides at positions 13, 15 and 19 in the nucleotide sequence shown in SEQ ID NO: 2. Further preferably, the sense strand may comprise 2'-substituted nucleotides at positions 2, 3, 4, 12, 13, 14, 17, 18 and 19 in the nucleotide sequence shown in SEQ ID NO: 1, and the antisense strand may comprise 2'-substituted nucleotides at positions 5, 13 and 15 in the nucleotide sequence shown in SEQ ID NO: 2. Yet further preferably, the sense strand may comprise 2'-substituted nucleotides at positions 2, 3, 4, 13, 17, 18 and 19 in the nucleotide sequence shown in SEQ ID NO: 1, and the antisense strand may comprise 2'-substituted nucleotides at positions 13, 15 and 19 in the nucleotide sequence shown in SEQ ID NO: 2. In these examples, the sense strand may comprise unmodified (natural type) nucleotide(s) at position(s) other than the above-described positions in the nucleotide sequence shown in SEQ ID NO: 1. The antisense strand may have unmodified (natural type) nucleotide(s) at position(s) other than the above-described positions in the nucleotide sequence shown in SEQ ID NO: 2.

The "2'-substituted nucleotide" means a nucleotide, in which the hydroxyl group at position 2' of sugar (ribose) constituting the nucleotide is replaced with another group. Since the siRNA comprises such 2'-substituted nucleotide(s), it is not an unmodified siRNA, but is a modified siRNA. The position 2' of the "2'-substituted nucleotide" is —$R^1$, —$OR^1$, —$R^2OR^1$, —$OR^2OR^1$, or —$R^3OR^2OR^1$, wherein $R^1$ represents a $C_{1-4}$ alkyl group, and $R^2$ and $R^3$ independently represent a $C_{1-3}$ alkylene group. The "alkyl group" means an optionally substituted, linear or branched, saturated or unsaturated, monovalent hydrocarbon group containing 1 to 4 carbon atoms. Examples of the "alkyl group" include a methyl group, an ethyl group, an n-propyl group, an isopropyl group, an n-butyl group, an isobutyl group, a sec-butyl group, and a tert-butyl group. The "alkylene group" means an optionally substituted, linear or branched, saturated or unsaturated, divalent hydrocarbon group containing 1 to 3 carbon atoms. Examples of the "alkylene group" include a methylene group, an ethylene group, and a trimethylene group. Examples of a substituent, which the alkyl group or the alkylene group may have, include a halogen atom (e.g., fluorine, chlorine, bromine, or iodine), an amino group, a nitro group, and a hydroxyl group. $R^1$ may be a $C_{1-3}$ alkyl group, a $C_{1-2}$ alkyl group, or a $C_1$ alkyl group. $R^2$ and $R^3$ may each be a $C_{1-2}$ alkylene group or a $C_1$ alkylene group. Specific examples of the substituent at position 2' of the 2'-substituted nucleotide include —$OCH_3$ (methoxy), —$OCH_2CH_3$ (ethoxy), —$OCH_2NH_2$ (aminomethoxy), —$OCH_2CH_2NH_2$ (aminoethoxy), —$OCH_2CH_2F$ (methylmethoxy fluoride), —$OCH_2CH_2CH_2F$ (methylethoxy fluoride), —$CH_3$ (methyl), —$CH_2CH_3$ (ethyl), —$CH_2CH_2CH_3$ (propyl), —$CH_2OCH_3$ (methoxymethyl; MOM), —$CH_2CH_2OCH_3$ (methoxyethyl; MOE), —$OCH_2OCH_3$, —$OCH_2CH_2OCH_3$, —$CH_2OCH_2OCH_3$, and —$CH_2OCH_2CH_2OCH_3$ (methoxy-ethoxymethyl; MEM), but the examples are not limited thereto. The 2'-substituted nucleotide is preferably a 2'-methoxy nucleotide (2'-O-methyl nucleotide) or a 2'-aminomethoxy nucleotide (2'-O-aminomethyl nucleotide). The siRNA comprising a 2'-methoxy nucleotide has lower stimulation to the innate immune system in a living body, than unmodified siRNA (see Judge, A D., et al. (2006) Mol. Ther., 13(3): 494-505; Robbins, M., et al. (2007) Mol. Ther., 15(9): 1663-1669; Sioud, M., (2006) Eur. J. Immunol., 36: 1222-1230). The sense strand and/or antisense strand which constitute the modified siRNA can comprise a plurality of 2'-substituted nucleotides as described above. The substituents at position 2' of such 2'-substituted nucleotides may be identical to or different from one another, and they are preferably identical to one another.

It has been generally known that, when the siRNA has a single-stranded portion (overhang) consisting of several (e.g., 2 to 5) nucleotides at the terminus thereof, it has high RNAi activity. As such, the siRNA preferably has an overhang consisting of several, modified or unmodified deoxyribonucleotides or ribonucleotides at the terminus thereof. In one example, the siRNA may have a 3'-overhang consisting of two nucleotides. The siRNA may preferably have a 3'-overhang consisting of dithymidylic acid (TT) or diuridylic acid (UU).

The sense strand and the antisense strand constituting the siRNA may each be 19 to 25 nucleotides in length. The sense strand and the antisense strand may have the same length as each other, or may have a different length from each other. That is to say, the sense strand may be constituted with the nucleotide sequence shown in SEQ ID NO: 1 (19 nucleotides in length), or may also have 1 to 6, for example, 1 to 4 or 1 or 2 deoxyribonucleotides or ribonucleotides (e.g., ribonucleotides homologous to RecQL1 mRNA, or UU or TT) at the 5'- or 3'-terminus thereof, and preferably, at the 3'-terminus thereof, in addition to the aforementioned sequence. On the other hand, the antisense strand may be constituted with the nucleotide sequence shown in SEQ ID NO: 2 (19 nucleotides in length), or may also have 1 to 6, for example, 1 to 4 or 1 or 2 deoxyribonucleotides or ribonucleotides (e.g., ribonucleotides complementary to RecQL1 mRNA, or UU or TT) at the 5'- or 3'-terminus thereof, and preferably, at the 3'-terminus thereof, in addition to the aforementioned sequence. The sense strand and the antisense strand are preferably 21 to 23 nucleotides in length, and more preferably 21 nucleotides in length.

The nucleotide sequence of the sense strand most preferably consists of the nucleotide sequence shown in SEQ ID NO: 1 (19 nucleotides in length) and TT (2 nucleotides in length) at the 3'-terminus (namely, the nucleotide sequence shown in SEQ ID NO: 3 (21 nucleotides in length)). On the other hand, the nucleotide sequence of the antisense strand most preferably consists of the nucleotide sequence shown in SEQ ID NO: 2 (19 nucleotides in length) and TT (2 nucleotides in length) at the 3'-terminus (namely, the nucleotide sequence shown in SEQ ID NO: 4 (21 nucleotides in length)). In these cases, the position of the 2'-substituted nucleotide can be indicated as a position counted from the 5'-terminal side of SEQ ID NO: 3 or 4. For example, positions 2, 3, 4 and 13 in the nucleotide sequence shown in SEQ ID NO: 1 can be indicated as positions 2, 3, 4 and 13 in the nucleotide sequence shown in SEQ ID NO: 3, respectively.

In the siRNA, not all nucleotides may necessarily be ribonucleotides (RNA). That is to say, one to several, for example, 1 to 4 ribonucleotides constituting the siRNA may be the corresponding deoxyribonucleotides. Preferably, the overhang of the siRNA may be composed of deoxyribonucleotides, and all other nucleotides may be ribonucleotides.

The siRNA may bind, at the 5'- and/or 3'-termini thereof, to a ligand molecule or a fluorescent molecule such as cholesterol, α-tocopherol, biotin, DIG, fluorescein, cyanine 3 (Cy3), or cyanine 5 (Cy5). Such binding may occur in the antisense strand and/or the sense strand. Preferably, the sense strand may bind to a ligand molecule or a fluorescent molecule at the 5'-terminus thereof and, more preferably, the sense strand may bind to cholesterol at the 5'-terminus thereof.

We had previously reported that mitotic catastrophe and mitotic cell death are induced to cancer cells by inhibition of the expression of a RecQL1 gene mediated by an RNAi mechanism involving siRNA (International Publication WO 2004/100990; International Publication WO 2006/054625; JP Patent Publication (Kokai) No. 2012-219085 A; Futami, K., et al. (2008) Cancer Sci., 99(1): 71-80; Futami, K., et al. (2008) Cancer Sci., 99(6): 1227-1236; and Futami, K., et al. (2010) Int. J. Mol. Med., 25: 537-545). Our modified siRNA targets a RecQL1 gene, and can induce cell death to cancer cells by inhibition of the expression of such a RecQL1 gene mediated by the RNAi mechanism. The modified siRNA may have higher cell death-inducing activity than unmodified siRNA having the same nucleotide sequence as that of the modified siRNA. The "unmodified siRNA" means siRNA (natural type siRNA) consisting of deoxyribonucleotides and/or ribonucleotides having no modifications on sugars, bases and phosphoric acid. The "cell death-inducing activity" of the siRNA can be easily determined by a person skilled in the art according to any of known methods. For example, as described in the after-mentioned Examples, siRNA is introduced into any given cancer cells (e.g., TOV-112D (ovarian cancer endometrioid adenocarcinoma) cells; ES-2 or TOV-21G (ovarian cancer clear cell adenocarcinoma) cells; HCT-15 (colorectal cancer) cells; A549 (lung cancer) cells; or HeLa (cervical cancer) cells), and the number of surviving cells (survival rate) is counted after a certain period of time (e.g., after approximately 72 to 120 hours) has passed so that the cell death-inducing activity of the siRNA can be determined. The number of surviving cells can be determined, for example, by a WST assay or count of the number of cells under a microscope.

The sense strand and the antisense strand constituting the modified siRNA can be produced by a common method well known in the art. The sense strand and the antisense strand can be produced, for example, by enzymatically or chemically synthesizing them in a manual or automatic reaction. When an RNA or DNA molecule is chemically synthesized, contract manufacturing service offered by manufacturers (e.g., GeneDesign, Inc., Dharmacon, QIAGEN, Sigma-Aldrich and the like) may be used. In such a case, the types and positions of 2'-substituted nucleotide(s), and the types and positions (5'- and/or 3'-termini) of ligand molecules or fluorescent molecules bound to the nucleotides as necessary, can be designated. The synthesized antisense strand and sense strand may be purified from a mixture, for example, according to extraction using a solvent or a resin, precipitation, electrophoresis, chromatography and the like. The modified siRNA can be produced by mixing the thus obtained sense strand and antisense strand, and annealing them to each other. It is also possible to obtain the annealed double-stranded siRNA from manufacturers.

The siRNA can be introduced into cells or tissues in vitro (ex vivo) or in vivo, or into an individual body in vivo, and then, it can be used to induce inhibition of the expression of the target gene RecQL1 via RNAi. Moreover, when the siRNA is introduced into cancer cells, it can induce cell death to the cancer cells by inhibition of the expression of the target gene RecQL1. Introduction of the siRNA can be carried out by a person skilled in the art according to a method known in the art. The siRNA may be introduced, for example, by physical methods such as direct injection of a solution containing the siRNA, bombardment using particles coated with the siRNA, or electroporation in the presence of the siRNA. Alternatively, the siRNA may be introduced by other methods for introducing a nucleic acid into cells which are known in the art such as lipid-mediated carrier transport or chemical-mediated transport (e.g., a calcium phosphate method), and further, the siRNA may also be introduced into cells by known drug delivery systems (DDS) such as liposome or polymeric micelles.

The applied dose of the siRNA in vitro can be appropriately determined by a person skilled in the art. For instance, the modified siRNA may be administered into cells such that the concentration thereof in a medium can be 0.01 to 100000 nM, 0.1 to 10000 nM, or 1 to 1000 nM. The dose of the siRNA in vivo will be described later in the section "Pharmaceutical composition."

Cells, tissues or individuals, into which the siRNA is to be introduced, may be those derived from primates (e.g., a rhesus monkey, a cynomolgus monkey, a chimpanzee and the like). Cells, tissues or individuals derived from humans are preferable.

Agents

We also provide an agent that inhibits RecQL1 gene expression, comprising the modified siRNA. "Inhibition of gene expression" means that the expression of the mRNA and/or protein of a target gene is inhibited by siRNA. The "inhibition of gene expression" does not only mean that the expression of a gene is inhibited by 100% relative to the case when siRNA is not introduced, when the expression level of the gene is determined using the expression level of the mRNA or protein of the gene as an indicator, but it also means that the expression of the gene is inhibited by 75% or more, 50% or more, 20% or more, or 10% or more. The degree of such gene expression inhibition can be determined using the expression level of the mRNA or protein of the target gene as an indicator. The expression level of mRNA can be determined by Northern hybridization, quantitative RT-PCR and the like, whereas the expression level of a protein can be determined by Western blotting, ELISA, the measurement of protein activity, the fluorescent intensity of a fluorescent protein or the like. Moreover, the "RNAi activity" of the siRNA may be determined based on the expression level of a RecQL1 gene (the expression level of mRNA or a protein), or may also be determined based on the cell death-inducing activity of the siRNA to cancer cells. The above-described agent for inhibiting RecQL1 gene expression comprises, as an active ingredient, the modified siRNA, and may also comprise other components such as pharmaceutically acceptable carriers or additives. The agent for inhibiting RecQL1 gene expression may be used as a research reagent (RNAi reagent), or may also be used as a pharmaceutical agent in the treatment of diseases.

We also provide an agent that induces cell death, comprising the modified siRNA. The agent that induces cell death does not induce cell death to normal cells, but can specifically induce cell death to cancer cells. The above-described agent that induces cell death comprises the modified siRNA as an active ingredient, and may also comprise other components such as pharmaceutically acceptable carriers or additives. The agent that induces cell death may be used as research reagents, or may also be used as a pharmaceutical agent in the treatment of diseases.

Pharmaceutical Composition

We further provide a pharmaceutical composition that treats cancer comprising, as an active ingredient, the modified siRNA.

Examples of the cancer to be treated include, but are not limited to, liver cancer, melanoma, breast cancer, ovarian cancer, lung cancer, colorectal cancer, stomach cancer, pancreatic cancer, bladder cancer, skin cancer, cervical cancer, prostate cancer, brain tumor, osteosarcoma, bile duct cancer, and head and neck cancer. In addition, ovarian cancer is generally classified into endometrioid adenocarcinoma, serous adenocarcinoma, clear cell adenocarcinoma, and mucinous adenocarcinoma.

The "treatment" means reduction or disappearance of cancer cells or tissues in a subject, or inhibition of the spread or progression of cancer.

The subject may be a primate (e.g., a rhesus monkey, a cynomolguss monkey, a chimpanzee and the like), and the subject is preferably a human.

The pharmaceutical composition can further comprise pharmaceutically acceptable carriers, as necessary. The pharmaceutically acceptable carriers include a diluent and an excipient, and specific examples of the pharmaceutically acceptable carriers include maltose, mannitol, lactose, xylose, trehalose, sorbitol, gelatin, gum Arabic, guar gum, tragacanth, ethanol, normal saline, and Ringer's solution.

The pharmaceutical composition may also comprise additives such as a stabilizer, a buffer agent, an emulsifier, a tonicity agent, and a preservative, as necessary, as well as the above-described carriers. These additives are preferably additives used upon drug manufacturing.

Examples of the stabilizer include albumin, gelatin, mannitol, and sodium EDTA. Examples of the buffer agent include sodium citrate, citric acid, and sodium phosphate. Examples of the emulsifier include sorbitan fatty acid ester and glycerin fatty acid ester. Examples of the tonicity agent include sodium chloride, potassium chloride, and sugars. Examples of the preservative include benzalkonium chloride, parahydroxybenzoic acid, and chlorobutanol.

The pharmaceutical composition can comprise other drugs, as long as the modified siRNA comprised as an active ingredient does not lose its RNAi activity. For example, in an injection, the pharmaceutical composition may comprise a predetermined amount of antibiotic.

Examples of the dosage form of the pharmaceutical composition include, but are not limited to, parenteral agents such as an injection, eye drops, a cream agent, nasal drops, an ointment, a transmucosal agent, plasters and a suppository, and oral agents such as a liquid agent, a powder agent, a tablet, a granule, a capsule, a sublingual tablet and lozenges.

The pharmaceutical composition can be administered to a living body in a therapeutically effective amount for the treatment of disease (cancer) of interest. The "therapeutically effective amount" means a dose necessary for the siRNA comprised in the pharmaceutical composition to treat cancer as a target, or to alleviate symptoms, wherein the dose causes almost no or completely no side effects that are harmful for a living body, to which the pharmaceutical composition is administered. The specific dose is determined depending on each subject, for example, by a physician's discretion, based on the progression or severity of disease, the healthy conditions of a whole body, age, body weight, sex, tolerability to the treatment and the like. For instance, the pharmaceutical composition may be administered to a subject such that the modified siRNA is administered in an amount of 0.0001 mg/kg of body weight/day to 10000 mg/kg of body weight/day, or 0.001 mg/kg of body weight/day to 1000 mg/kg of body weight/day, or 0.01 mg/kg of body weight/day to 100 mg/kg of body weight/day.

Administration of the pharmaceutical composition may be either systemic administration or local administration (e.g., direct administration to affected area). The administration route may be either parenteral or oral administration. Examples of the administration route include intraperitoneal, intravenous, intraarterial, intrahepatic, intravaginal, intramuscular, intramedullary, intraspinal, transdermal, subcutaneous, intradermal, intranasal, intraintestinal, intrabronchial, intrapulmonary, and sublingual administrations.

Moreover, the pharmaceutical composition can be administered to a patient, for example, based on a therapeutic plan determined by a physician, at certain time intervals, for example, at intervals of 1 day, 2 days, 3 days, 4 days, 5 days, 6 days, 1 week, 2 weeks, 3 weeks, 1 month, 2 months, 6 months, 1 year, or the like, at once, or divided over several to several tens of administrations.

Method

We further provide a method of inhibiting the expression of a RecQL1 gene, a method of inducing cell death to cells, or a method of treating cancer, in which the above-described agent or composition comprising the modified siRNA is used. These methods may be in vitro methods, ex vivo methods, or in vivo methods.

EXAMPLES

Hereinafter, our modified siRNA, pharmaceutical compositions and methods will be further specifically described in the following examples. However, these examples are not intended to limit the technical scope of this disclosure.

Example 1

In Vitro RNAi Activity of Modified RecQL1-siRNA

We examined in vitro the RNAi activity of modified RecQL1-siRNA comprising 2'-substituted nucleotide(s) at different positions, using various cell lines.

Materials and Methods

Preparation of Cells

The cells of the following human cell lines were used in experiments: TOV-112D (ovarian cancer endometrioid adenocarcinoma), ES-2 and TOV-21G (ovarian cancer clear cell adenocarcinoma), HCT-15 (colorectal cancer), A549 (lung cancer), and HeLa (cervical cancer) cells. These cell lines were acquired from ATCC (American Type Culture Collection). One day before siRNA transfection, the cells of these cell lines were plated at a cell density of $2.0 \times 10^4$ cells per well on a 24-well plate, or $2.0 \times 10^3$ cells per well on a 96-well microplate. Thereafter, the cells were cultured using the following culture media: DMEM (Nacalai Tesque, Inc.)+10% FBS (fetal bovine serum, Sigma-Aldrich)+1% penicillin/streptomycin (GIBCO) for TOV-112D, TOV-21G and HeLa; McCoy5A (Gibco BRL)+10% FBS+1% penicillin/streptomycin for ES-2; RPMI (Nacalai Tesque, Inc.)+10%

FBS+penicillin/streptomycin for HCT-15; and EMEM (Wako Pure Chemical Industries, Ltd.)+10% FBS+NEAA (non-essential amino acids, Wako Pure Chemical Industries, Ltd.)+penicillin/streptomycin for A549.

siRNA Transfection

The synthesis of siRNA was conducted by GeneDesign, Inc. The nucleotide sequences of the used siRNAs and modification positions are shown in FIG. 1. The used siRNAs target positions 273 to 291 of a human RecQL1 gene coding region (SEQ ID NO: 19). Individual modified RecQL1-siRNAs (FIGS. 1B to 1J) have the same nucleotide sequence as that of unmodified RecQL1-siRNA (FIG. 1A), but they comprise 2'-methoxy nucleotides (2'-O-methyl nucleotides) at positions as shown in FIG. 1. In addition, modified siRNA (QL-19-Chol) prepared by binding cholesterol to the 5'-terminus of the sense strand of the modified siRNA, QL-19 (FIG. 1G), was used. As a negative control that did not exhibit RNAi activity, GL3-siRNA or mGL3-siRNA was used. The GL3-siRNA is an unmodified polynucleotide chain having the following nucleotide sequences: 5'-CUUACGCUGAGUACUUCGATT-3' (SEQ ID NO: 17) and 5'-UCGAAGUACUCAGCGUAAGTT-3' (SEQ ID NO: 18). On the other hand, the mGL3-siRNA has the same nucleotide sequence as that of GL3-siRNA, but comprises several 2'-methoxy nucleotides. The sequences thereof are shown in SEQ ID NOs: 21 and 22.

Individual siRNAs at a concentration of interest (1, 2.5, 5, 10, 25 or 50 nM in the experiment shown in FIG. 2; 1, 2.5, 5, 10 or 25 nM in the experiments shown in FIGS. 3 to 7; 1, 2.5, 5 or 25 nM in the experiments shown in FIGS. 8 and 9; and 1.3 nM in the experiment shown in FIG. 10) were each introduced into cells, using Lipofectamine™ RNAiMAX Reagent (Invitrogen), basically in accordance with protocols provided by the manufacturer. In the experiments shown in FIGS. 11A and 11B, siRNA was introduced into cells by being directly added to a culture medium to a concentration of 500 nM. In the experiment shown in FIG. 11C, siRNA was introduced into cells by being directly added to a culture medium to a concentration of 250 nM. As necessary, approximately 48 hours after the siRNA transfection, the cells were appropriately diluted not to reach confluence, and were then plated again.

Cell Death-inducing Activity

Ninety-six hours after the siRNA transfection (FIGS. 2, 8 and 9) or 120 hours after the siRNA transfection (FIGS. 3 to 7), the number of living cells was determined by a WST assay using a live cell count reagent SF (Nacalai Tesque, Inc.). The assay was carried out in accordance with protocols provided by the manufacturer. The ratio of the determined living cell number to the determined living cell number in non-transfected cells (survival rate (%)) was calculated. Using the survival rate as an indicator, the cell death-inducing activity was evaluated.

Gene Expression-inhibiting Activity

Figure 10:
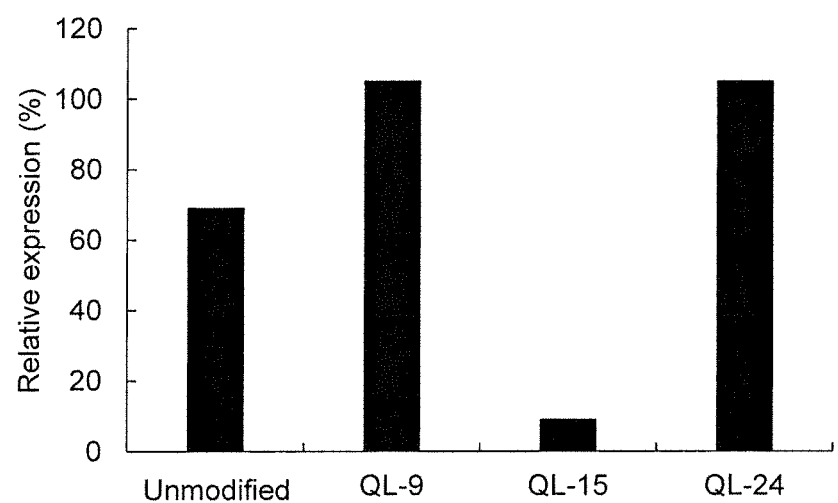
FIG. 10 is a graph showing the RecQL1 gene expression-inhibiting activity of modified RecQL1-siRNA (QL-15) to HeLa (cervical cancer) cells.

Thirty hours (FIG. 10) or twenty-hour hours (FIG. 11) after the siRNA transfection, the cells were recovered, and total RNA was then extracted from the recovered cells using NucleoZOL (MACHERY-NAGEL). The amount of RecQL1 mRNA (the expression level of the RecQL1 gene) in the extracted RNA was determined by quantitative RT-PCR. The quantitative RT-PCR was carried out using Rotor-Gene Q 2plex System (QIAGEN). RT-PCR primers and TaqMan probes for RecQL1 and β-actin genes were purchased from Applied Biosystems. The RT-PCR reaction was carried out using QuantiFast Probe RT-PCR Kit (QIAGEN), in accordance with the instruction manual included therewith. The expression level of the RecQL1 gene was normalized with respect to the expression level of the β-actin gene. In the experiment, the results of which are shown in FIG. 10, relative expression (%) was calculated, using, as a reference (100%), the expression level in non-transfected cells. On the other hand, in the experiment, the results of which are shown in FIG. 11, relative expression (%) was calculated, using, as a reference (100%), the expression level in cells transfected with the modified RecQL1-siRNA QL-19. Using such relative expression as an indicator, the gene expression-inhibiting activity was evaluated.

Results

The RNAi activity of modified siRNAs (QL-15, QL-16 and QL-17; FIGS. 1C to 1E), in which some of C and U in the sense strand were 2'-methoxylated, was examined. The C and U at positions 8 and 9 in the sense strand of QL-15 were unmodified, and the C and U at positions 2, 3, 4, 11, 12, 13, 14, 17, 18 and 19 were 2'-methoxylated. The C and U at positions 17, 18 and 19 in the sense strand of QL-16 were unmodified, and the C and U at positions 2, 3, 4, 8, 9, 11, 12, 13 and 14 were 2'-methoxylated. The C and U at positions 8, 9, 17, 18 and 19 in the sense strand of QL-17 were unmodified, and the C and U at positions 2, 3, 4, 11, 12, 13 and 14 were 2'-methoxylated. We previously reported that mitotic catastrophe and mitotic cell death are induced to cancer cells by inhibition of the expression of a RecQL1 gene mediated by an RNAi mechanism involving siRNA (International Publication WO 2004/100990; International Publication WO 2006/054625; JP Patent Publication (Kokai) No. 2012-219085 A; Futami, K., et al. (2008) Cancer Sci., 99(1): 71-80; Futami, K., et al. (2008) Cancer Sci., 99(6): 1227-1236; and Futami, K., et al. (2010) Int. J. Mol. Med., 25: 537-545). Hence, the RNAi activity of the above-described modified siRNAs was evaluated based on their cell death-inducing activity.

As a result, all of QL-15, QL-16 and QL-17 surprisingly exhibited higher RNAi activity on ES-2 (ovarian cancer clear cell adenocarcinoma) cells, than unmodified siRNA (FIG. 2). In particular, QL-15 and QL-17 exhibited high RNAi activity. QL-15 exhibited the highest RNAi activity. Moreover, these results showed that when positions 8 and 9 in the sense strand are unmodified (QL-15 and QL-17), much higher RNAi activity can be obtained.

Subsequently, the RNAi activity of modified siRNAs (QL-18, QL-19, QL-20 and QL-21; FIGS. 1F to 1I), in which 2'-methoxy nucleotides were comprised in both the sense strand and the antisense strand, was examined. QL-18 to QL-20 comprise 2'-methoxy nucleotides at positions 2, 3, 4, 12, 13, 14, 17, 18 and 19 in the sense strand thereof. QL-21 comprises 2'-methoxy nucleotides at positions 2, 3, 4, 13, 17, 18 and 19 in the sense strand thereof. On the other hand, with regard to the antisense strand, QL-18 comprises 2'-methoxy nucleotides at positions 5, 13, 15 and 19 in the antisense strand thereof. QL-19 and QL-21 comprise 2'-methoxy nucleotides at positions 13, 15 and 19 in the antisense strand thereof. QL-20 comprises 2'-methoxy nucleotides at positions 5, 13 and 15 in the antisense strand thereof.

Figure 4A:
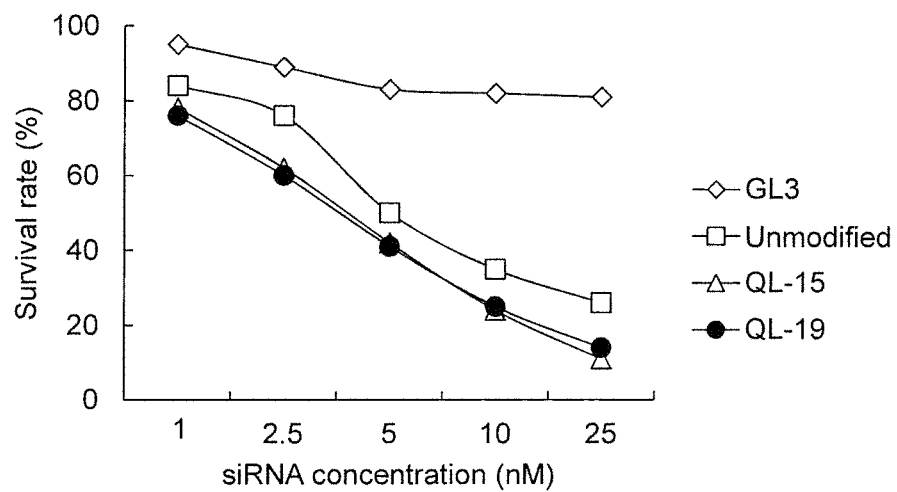
FIGS. 4A and 4B are graphs showing the cell death-inducing activity of modified RecQL1-siRNA (QL-19). The activity to (A) TOV-112D (ovarian cancer endometrioid adenocarcinoma) and (B) ES-2 (ovarian cancer clear cell adenocarcinoma) cells is shown.
Figure 4B:
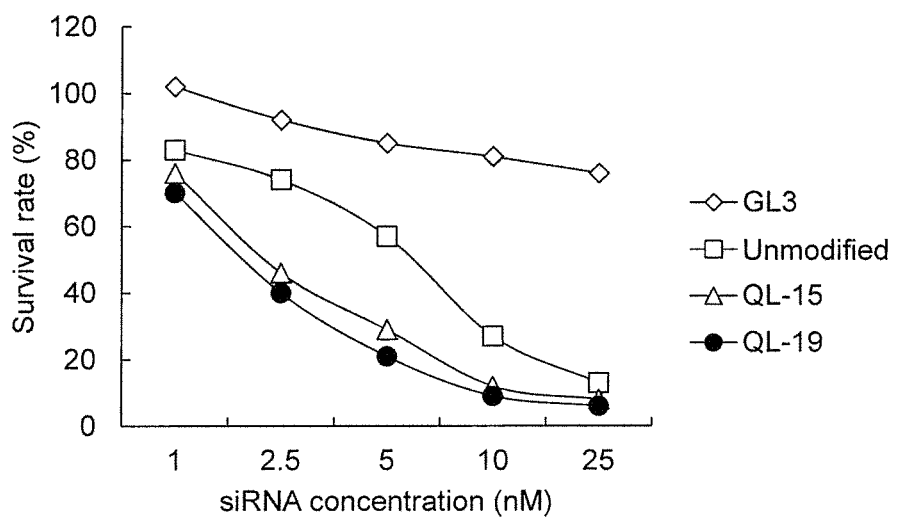
Figure 5A:
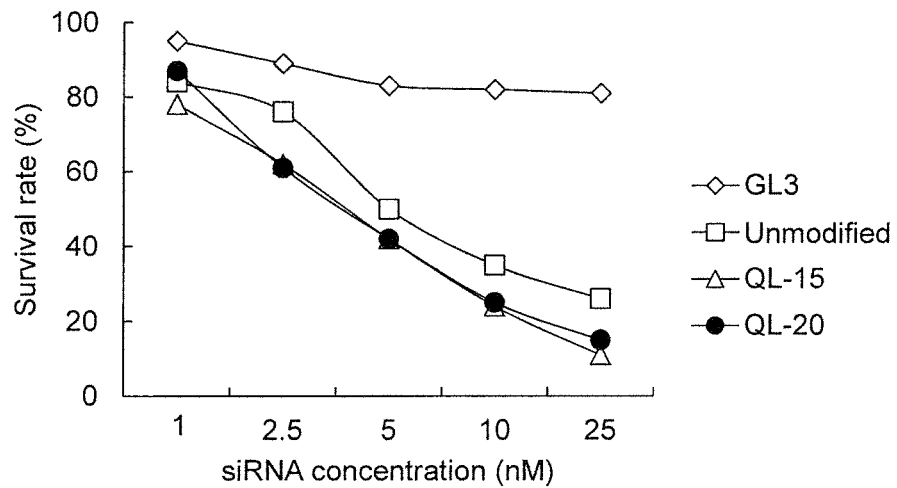
FIGS. 5A and 5B are graphs showing the cell death-inducing activity of modified RecQL1-siRNA (QL-20). The activity to (A) TOV-112D (ovarian cancer endometrioid adenocarcinoma) and (B) ES-2 (ovarian cancer clear cell adenocarcinoma) cells is shown.
Figure 5B:
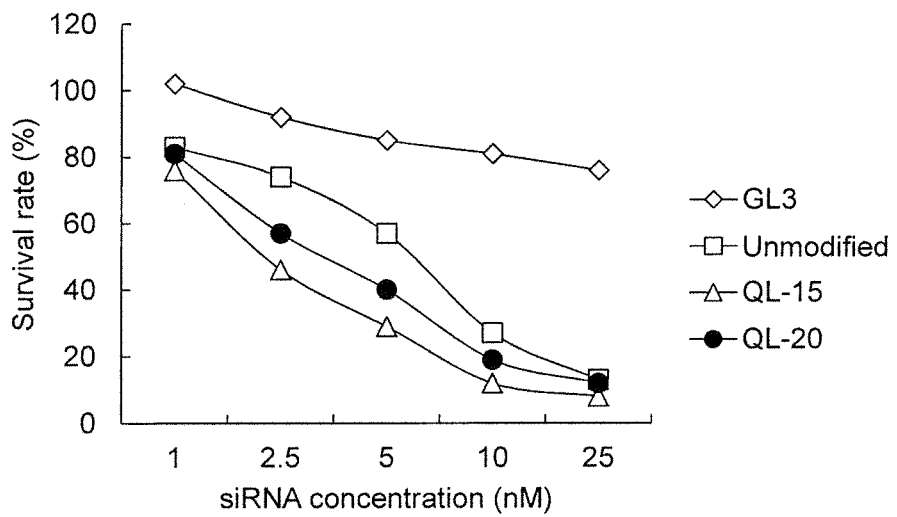
Figure 6A:
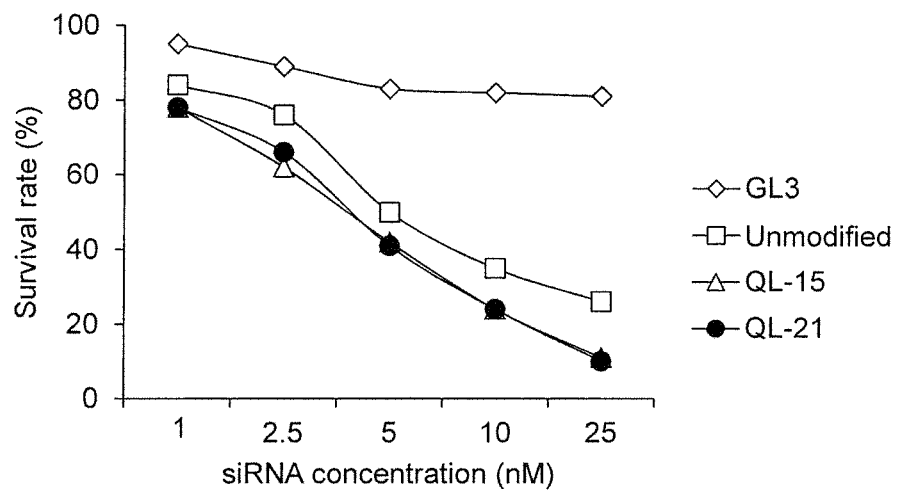
FIGS. 6A and 6B are graphs showing the cell death-inducing activity of modified RecQL1-siRNA (QL-21). The activity to (A) TOV-112D (ovarian cancer endometrioid adenocarcinoma) and (B) ES-2 (ovarian cancer clear cell adenocarcinoma) cells is shown.
Figure 6B:
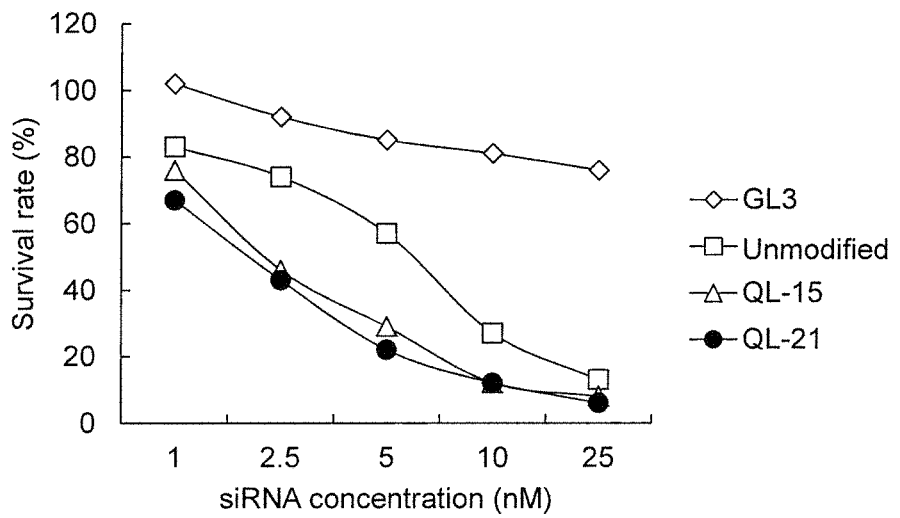

As a result, all of QL-18 to QL-21 tended to have higher RNAi activity on ovarian cancer cells, namely, TOV-112D (ovarian cancer endometrioid adenocarcinoma) and ES-2 (ovarian cancer clear cell adenocarcinoma), than unmodified siRNA (FIGS. 3 to 6). In particular, QL-19 and QL-21 had high RNAi activity on the two above types of cells, and QL-19 had the highest activity (FIGS. 4 and 6).

Figure 7:
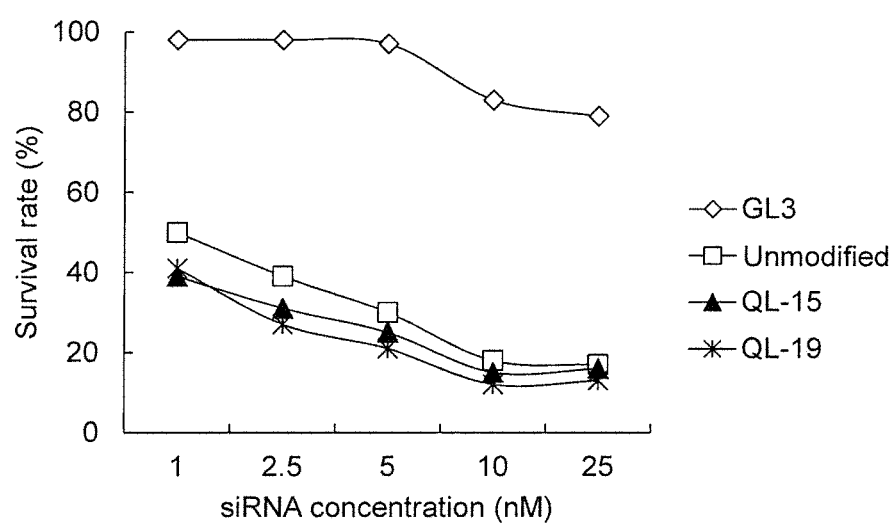
FIG. 7 is a graph showing the cell death-inducing activity of modified RecQL1-siRNAs (QL-15 and QL-19) to TOV-21G (ovarian cancer clear cell adenocarcinoma) cells.
Figure 8:
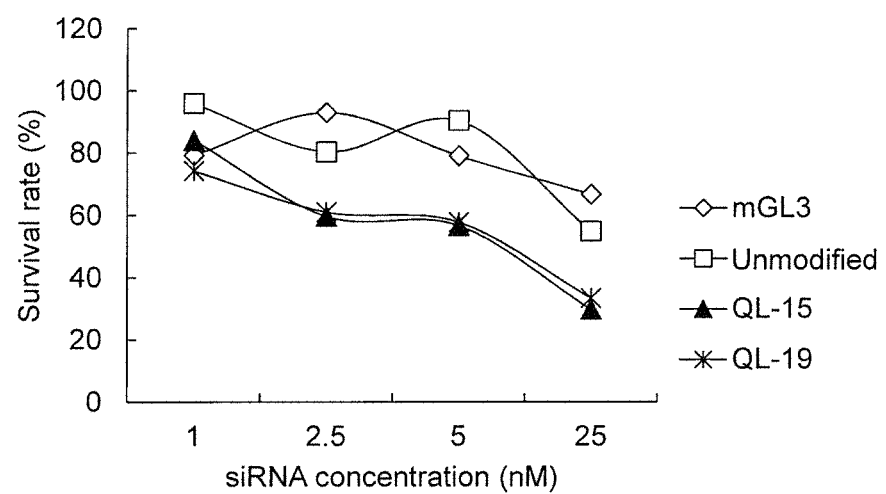
FIG. 8 is a graph showing the cell death-inducing activity of modified RecQL1-siRNAs (QL-15 and QL-19) to HCT-15 (colorectal cancer) cells.
Figure 9:
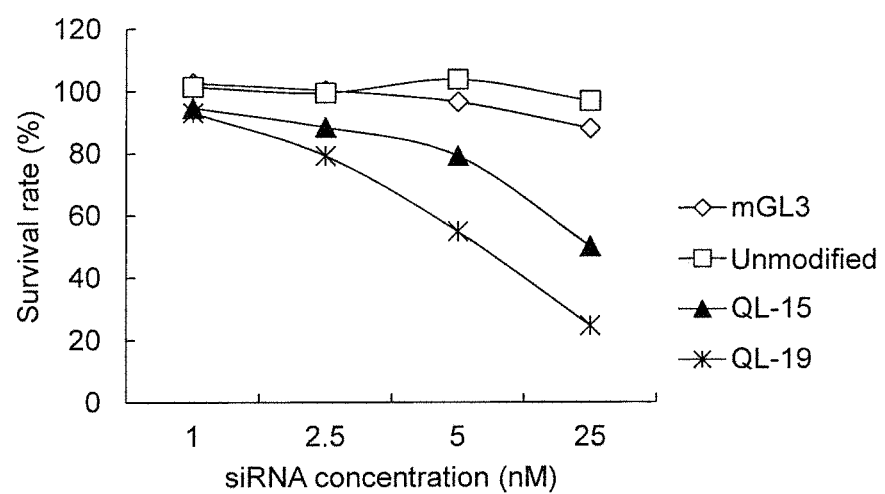
FIG. 9 is a graph showing the cell death-inducing activity of modified RecQL1-siRNAs (QL-15 and QL-19) to A549 (lung cancer) cells.

With regard to QL-15 and QL-19 exhibiting particularly high RNAi activity in the aforementioned experiments, their activity on TOV-21G (ovarian cancer clear cell adenocarcinoma), HCT-15 (colorectal cancer), and A549 (lung cancer) was further examined. As a result, it was demonstrated that QL-15 and QL-19 had higher RNAi activity on all of the aforementioned cells, than unmodified siRNA (FIGS. 7 to 9).

Thereafter, using HeLa (cervical cancer) cells, the gene expression-inhibiting activity of modified siRNAs (QL-9, QL-15 and QL-24; FIGS. 1B, 1C and 1J), which had 2'-methoxy nucleotides at various positions in the sense strand and had an unmodified antisense strand, was examined. The all C and U (at positions 2, 3, 4, 8, 9, 11, 12, 13, 14, 17, 18 and 19) in the sense strand of QL-9 were 2'-methoxylated. As mentioned above, the C and U in the sense strand of QL-15 were 2'-methoxylated at positions 2, 3, 4, 11, 12, 13, 14, 17, 18 and 19. The C and U in the sense strand of QL-24 were 2'-methoxylated at positions 2, 3, 4, and 13. The results are shown in FIG. 10. Both QL-9 and QL-24 had lower gene expression-inhibiting activity than unmodified siRNA, whereas QL-15 had significantly higher gene expression-inhibiting activity than unmodified siRNA (FIG. 10). It has been generally known that 2'-methylation of nucleotides improves nuclease resistance. On the other hand, it has also been known that the RNAi activity of siRNA is generally reduced by 2'-methoxylation of nucleotides. Based on such general knowledge, it has been totally unexpected that the siRNA according to one example in which nucleotides at specific positions have been 2'-methoxylated has higher RNAi activity than unmodified siRNA. It is suggested that an unknown mechanism which is irrelevant to the improvement of nuclease resistance by 2'-methoxylation enhances the RNAi activity of our siRNA.

Figure 11A:
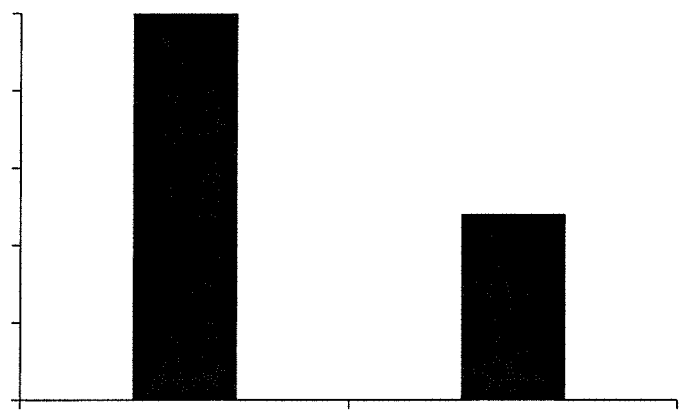
FIGS. 11A-11C are graphs showing the RecQL1 gene expression-inhibiting activity of siRNA (QL-19-Chol) formed by binding cholesterol to modified RecQL1-siRNA (QL-19), to (A) A549 (lung cancer) cells, (B) HeLa (cervical cancer) cells, or (C) ES-2 (ovarian cancer clear cell adenocarcinoma) cells.
Figure 11B:
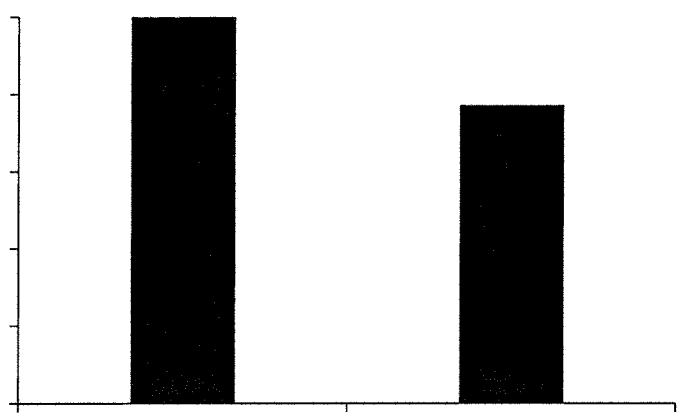
Figure 11C:
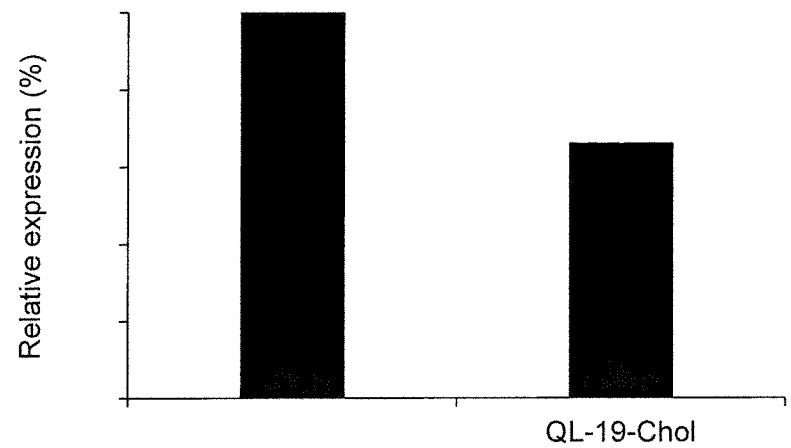

Subsequently, using A549 (lung cancer) cells, HeLa (cervical cancer) cells or ES-2 (ovarian cancer clear cell adenocarcinoma) cells, the above 2'-methoxylated siRNA (QL-19) was compared with QL-19 (QL-19-Chol), to the 5'-terminus of the sense strand of which cholesterol binds, in terms of gene expression-inhibiting activity. FIGS. 11A to C show the results obtained using A549 (lung cancer) cells, HeLa (cervical cancer) cells, or ES-2 (ovarian cancer clear cell adenocarcinoma) cells, respectively. QL-19-Chol had higher gene expression-inhibiting activity than QL-19, on all types of cells. Thus, it was demonstrated that, by binding cholesterol to the 5'-terminus of the sense strand of siRNA, the siRNA can be efficiently introduced into cells without using another drug delivery system (DDS), and thus that certain gene expression-inhibiting activity of the siRNA can be maintained (FIG. 11).

To sum up, modified RecQL1-siRNA, which has higher RNAi activity than unmodified RecQL1-siRNA, and comprises 2'-substituted nucleotides (2'-methoxy nucleotides) in only the sense strand thereof (QL-15, QL-16 and QL-17), or in both the sense strand and the antisense strand (QL-18, QL-19, QL-20 and QL-21), was discovered. Moreover, it was also found that the pyrimidine nucleotides (C or U) at positions 2, 3, 4 and 13 in the sense strands of these modified RecQL1-siRNAs are always 2'-methoxylated, and that pyrimidine nucleotides at other positions are further 2'-methoxylated. Furthermore, it was demonstrated that, by binding cholesterol to the 5'-terminus of the sense strand of modified RecQL1-siRNA comprising 2'-substituted nucleotides, the siRNA exhibits RNAi activity without using another DDS.

Besides, when all of U and C in the two RNA strands (an antisense strand and a sense strand) were substituted with 2'-methoxylated nucleotides, the RNAi effects tended to be reduced.

Example 2

Inhibition of Growth of Tumor Cells in Cancer-bearing Animal Models by Modified RecQL1-siRNA We examined whether or not the modified RecQL1-siRNA (QL-19), which had been demonstrated to have high RNAi activity in vitro in Example 1, had the effects even in vivo, using cancer-bearing animal models.

Materials and Methods
Preparation of Cancer-bearing Mice

TOV-112D cells (human ovarian cancer endometrioid adenocarcinoma, grade 3, stage IIIc; acquired from ATCC) were sub-cultured in a DMEM medium (Nacalai Tesque, Inc.) containing 10% FBS (Sigma-Aldrich) and 1% penicillin/streptomycin in an incubator of 37° C. at a confluency of 80% or less. Thereafter, the cells were washed with PBS, and were then recovered by being dissociated in 0.05% trypsin-EDTA (Nacalai Tesque, Inc.). The recovered cells were centrifuged at 300×g for 3 minutes at 4° C. The precipitated cells were suspended in cold PBS to a cell density of $2\times10^7$ cells/ml to obtain a TOV-112D cell suspension.

Four-week-old female Balb/c nude mice (CAnN.Cg-Foxn1$^{nu}$/CrlCrlj) were purchased from Charles River Laboratories Japan, Inc. The mice were acclimated for 1 week. Thereafter, 500 µl of the above-described TOV-112D cell suspension was intraperitoneally administered to the five-week-old mice so that the cells were transplanted into the mice, thereby preparing cancer-bearing mice.

Administration of siRNA

As siRNAs, GL3-siRNA and mGL3-siRNA (described in Example 1), unmodified RecQL1-siRNA (FIG. 1A), and modified RecQL1-siRNA (QL-19; FIG. 1G) were used. Each siRNA was mixed with LIC-101 (Nippon Shinyaku Co., Ltd.) at a ratio of 1:16 (w/w) to obtain a liposome solution of siRNA (1 mg/ml). This liposome solution was diluted with a 10% maltose solution (Otsuka Pharmaceutical Co., Ltd.). Administration of siRNA (at a dose of 3.75 mg/kg) or only the vehicle (10% maltose) was initiated on the 3rd day or the 7th day after transplantation of TOV-112D (ovarian cancer endometrioid adenocarcinoma) cells into mice, and the siRNA or the vehicle was intraperitoneally administered to the cancer-bearing mice (10 mice per group) every two days, 10 times.

Measurement of Tumor Weight

The mice were subjected to dissection on the 23rd or 24th day after the transplantation of TOV-112D (ovarian cancer endometrioid adenocarcinoma) cells. The peritoneum including the digestive tracts from the esophagus to the rectum was excised from each mouse. Thereafter, the digestive tracts were excised from the peritoneum, and the weight of the peritoneum was measured. In addition, the ratio (%) of the weight of the peritoneum to the body weight of a mouse was calculated.

Results

Figure 12A:
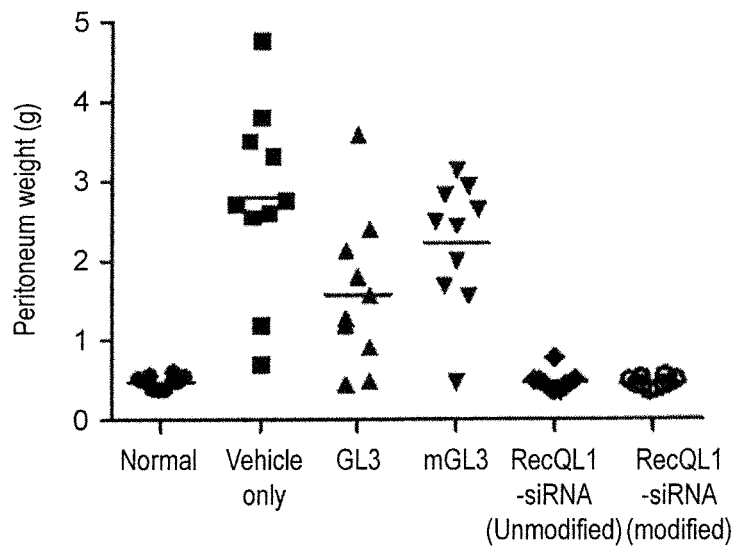
FIGS. 12A and 12B are graphs showing the tumor cell growth-inhibiting activity of modified RecQL1-siRNA (QL-19), the administration of which has been initiated on the 3rd day after transplantation. (A) shows peritoneum weight (g) and (B) shows the percentage (%) of peritoneum weight to body weight.
Figure 12B:
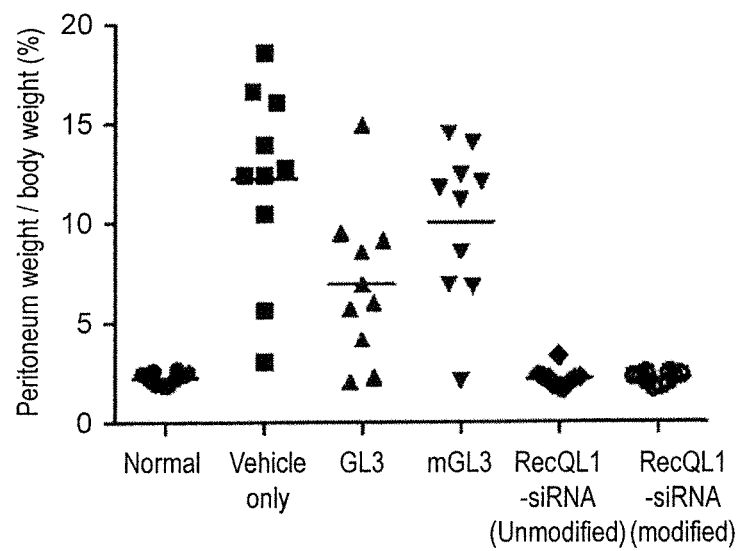
Figure 13A:
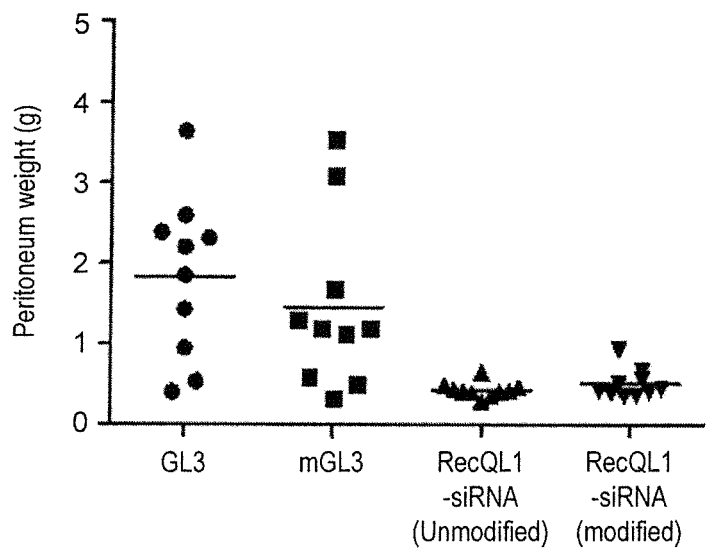
FIGS. 13A and 13B are graphs showing the tumor cell growth-inhibiting activity of modified RecQL1-siRNA (QL-19), the administration of which has been initiated on the 7th day after transplantation. (A) shows peritoneum weight (g) and (B) shows the percentage (%) of peritoneum weight to body weight.
Figure 13B:
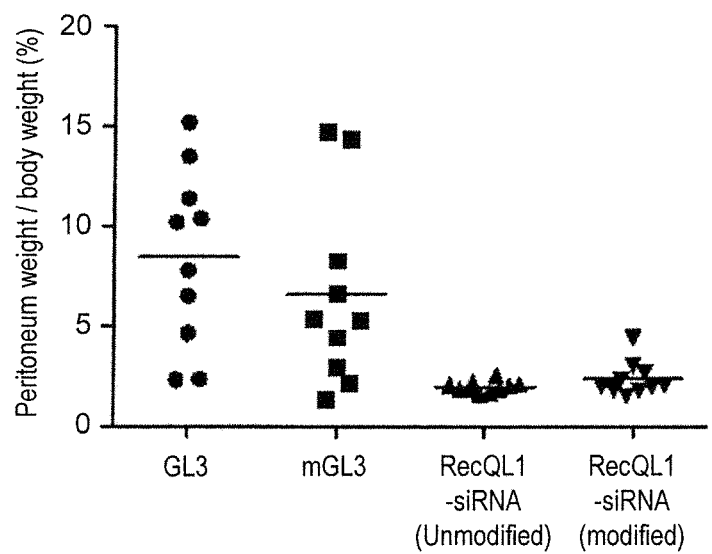

Even when administration of siRNA to mice was initiated on the 3rd day (FIG. 12) or on the 7th day (FIG. 13) after transplantation of the cancer cells into the mice, an increase in the peritoneum weight associated with tumor nodule formation and tumor proliferation was significantly inhibited by unmodified RecQL1-siRNA or modified RecQL1-siRNA.

From the aforementioned results, it was demonstrated that the modified RecQL1-siRNA (QL-19) has the effect of greatly inhibiting proliferation of tumor cells in vivo.

Comparative Example

In the sense strand and the antisense strand of QL-2S, QL-3S and QL-5, nucleotides at specific positions were 2'-methoxylated, but positions 2, 3 and 13 of the sense strand thereof were unmodified (FIG. 14). All of QL-2S, QL-3 S and QL-5 exhibited lower RNAi activity than unmodified siRNA having the same sequence.

INDUSTRIAL APPLICABILITY

The modified RecQL1-siRNA is predicted not to have off-target effects on genes other than a RecQL1 gene and, further, the modified RecQL1-siRNA does not induce cell death to normal cells, and specifically induces cell death to cancer cells. Therefore, it is expected that the modified RecQL1-siRNA will be used as a practical pharmaceutical agent having only a few side effects.

SEQUENCE LISTING FREE TEXT

SEQ ID NOs: 1 and 2: Synthetic oligonucleotides
SEQ ID NOs: 3 to 18 and 21 to 24: Conjugated DNA/RNA molecules: synthetic oligonucleotides All publications, patents and patent applications cited in this description are incorporated herein by reference in their entirety.

The invention claimed is:

1. Double-stranded modified siRNA targeting a RecQL1 helicase gene comprising:
   a sense strand comprising the nucleotide sequence shown in SEQ ID NO: 1, and
   an antisense strand comprising the nucleotide sequence shown in SEQ ID NO: 2, wherein
   the sense strand comprises 2'-substituted nucleotides at positions 2, 3, 4 and 13 in the nucleotide sequence shown in SEQ ID NO: 1 when the nucleotide at the 5' end of the nucleotide sequence is position 1,
   the sense strand further comprises a 2'-substituted nucleotide(s) at one or more positions selected from the group consisting of positions 12, 14, 17, 18 and 19 in the nucleotide sequence shown in SEQ ID NO: 1 when the nucleotide at the 5' end of the nucleotide sequence is position 1, and
   the 2'-substituted nucleotide is a 2'-methoxy nucleotide, and
   the positions of the 2'-substituted nucleotides in the sense strand of the nucleotide sequence shown in SEQ ID NO: 1 are:
   (a) positions 2, 3, 4, 11, 12, 13, 14, 17, 18 and 19,
   (b) positions 2, 3, 4, 11, 12, 13 and 14,
   (c) positions 2, 3, 4, 12, 13, 14, 17, 18 and 19, or
   (d) positions 2, 3, 4, 13, 17, 18 and 19.

2. The modified siRNA according to claim 1, having a higher cell death-inducing activity than unmodified siRNA having the same nucleotide sequence.

3. The modified siRNA according to claim 1, wherein the antisense strand is not modified.

4. The modified siRNA according to claim 1, wherein the antisense strand comprises the 2'-substituted nucleotides at positions in the nucleotide sequence shown in SEQ ID NO: 2:
   (i) positions 13, 15 and 19,
   (ii) positions 5, 13, 15 and 19, or
   (iii) positions 5, 13, and 15.

5. The modified siRNA according to claim 1, comprising a 3'-overhang consisting of TT or UU.

6. The modified siRNA according to claim 1, wherein the sense strand and the antisense strand each are 19 to 25 nucleotides in length.

7. The modified siRNA according to claim 1, wherein the sense strand has cholesterol bound at the 5'-terminus thereof.

8. An agent inhibiting RecQL1 gene expression, comprising the modified siRNA according to claim 1.

9. An agent that induces cell death comprising the modified siRNA according to claim 1.

10. A pharmaceutical composition that treats a RecQL1 gene expressing cancer comprising the modified siRNA according to claim 1.

11. The pharmaceutical composition according to claim 10, wherein the cancer is ovarian cancer, breast cancer, melanoma, liver cancer, colorectal cancer, lung cancer, or cervical cancer.

* * * * *

SEQUENCE LISTING

```
<160> NUMBER OF SEQ ID NOS: 24

<210> SEQ ID NO 1
<211> LENGTH: 19
<212> TYPE: RNA
<213> ORGANISM: Artificial
<220> FEATURE:
<223> OTHER INFORMATION: Synthetic oligonucleotide

<400> SEQUENCE: 1
guucagacca cuucagcuu                                                  19

<210> SEQ ID NO 2
<211> LENGTH: 19
<212> TYPE: RNA
<213> ORGANISM: Artificial
<220> FEATURE:
<223> OTHER INFORMATION: Synthetic oligonucleotide

<400> SEQUENCE: 2
aagcugaagu ggucugaac                                                  19

<210> SEQ ID NO 3
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

<400> SEQUENCE: 3
guucagacca cuucagcuut t                                               21

<210> SEQ ID NO 4
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

<400> SEQUENCE: 4
aagcugaagu ggucugaact t                                               21

<210> SEQ ID NO 5
<211> LENGTH: 21
<212> TYPE: DNA
```

<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (8)..(9)
<223> OTHER INFORMATION: cm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: um
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(19)
<223> OTHER INFORMATION: um

<400> SEQUENCE: 5
guucagacca cuucagcuut t                                           21

<210> SEQ ID NO 6
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (12)..(13)
<223> OTHER INFORMATION: um
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (17)..(17)
<223> OTHER INFORMATION: cm -continued

```
<220> FEATURE:
<221> NAME/KEY: modified_base
<222> LOCATION: (18)..(19)
<223> OTHER INFORMATION: um

<400> SEQUENCE: 6
guucagacca cuucagcuut t                                              21

<210> SEQ ID NO 7
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (8)..(9)
<223> OTHER INFORMATION: cm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: um
<220> FEATURE:
<221> NAME/KEY: modified_base
<222> LOCATION: (14)..(14)
<223> OTHER INFORMATION: cm

<400> SEQUENCE: 7
guucagacca cuucagcuut t                                              21

<210> SEQ ID NO 8
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: um
```

```
<220> FEATURE:
<221> NAME/KEY: modified_base
<222> LOCATION: (14)..(14)
<223> OTHER INFORMATION: cm

<400> SEQUENCE: 8
guucagacca cuucagcuut t                                              21

<210> SEQ ID NO 9
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 9
aagcugaagu ggucugaact t                                              21

<210> SEQ ID NO 10
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 10
aagcugaagu ggucugaact t                                              21

<210> SEQ ID NO 11
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
```

```
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: um

<400> SEQUENCE: 11
aagcugaagu ggucugaact t                                              21

<210> SEQ ID NO 12
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(19)
<223> OTHER INFORMATION: um

<400> SEQUENCE: 12
guucagacca cuucagcuut t                                              21

<210> SEQ ID NO 13
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (9)..(9)
<223> OTHER INFORMATION: cm
```

```
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (18)..(18)
<223> OTHER INFORMATION: um

<400> SEQUENCE: 13
guucagacca cuucagcuut t                                              21

<210> SEQ ID NO 14
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 14
aagcugaagu ggucugaact t                                              21

<210> SEQ ID NO 15
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (4)..(4)
<223> OTHER INFORMATION: cm
```

```
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: cm

<400> SEQUENCE: 15
guucagacca cuucagcuut t                                               21

<210> SEQ ID NO 16
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: cm

<400> SEQUENCE: 16
guucagacca cuucagcuut t                                               21

<210> SEQ ID NO 17
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

<400> SEQUENCE: 17
cuuacgcuga guacuucgat t                                               21

<210> SEQ ID NO 18
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA

<400> SEQUENCE: 18
ucgaaguacu cagcguaagt t                                               21
```

<210> SEQ ID NO 19
<211> LENGTH: 1950
<212> TYPE: DNA
<213> ORGANISM: Homo sapiens

<400> SEQUENCE: 19

| | | | | | |
|---|---|---|---|---|---|
| atggcgtccg | tttcagctct | aactgaggaa | ctggattcta | taaccagtga | gctacatgca | 60 |
| gtagaaattc | aaattcaaga | acttacggaa | aggcaacaag | agcttattca | gaaaaaaaaa | 120 |
| gtcctgacaa | agaaaataaa | gcagtgttta | gaggattctg | atgccggggc | aagcaatgaa | 180 |
| tatgattctt | cacctgccgc | ttggaataaa | gaagattttc | catggtctgg | taaagttaaa | 240 |
| gatattctgc | aaaatgtctt | taaactggaa | aagttcagac | cacttcagct | tgaaactatt | 300 |
| aacgtaacaa | tggctggaaa | ggaggtattt | cttgttatgc | ctacaggagg | tggaaagagc | 360 |
| ttatgttacc | agttaccagc | attatgttca | gatggtttta | cactcgtcat | ttgcccattg | 420 |
| atctctctta | tggaagacca | attaatggtt | ttaaaacaat | taggaatttc | agcaaccatg | 480 |
| ttaaatgctt | ctagttctaa | ggagcatgtt | aaatgggttc | atgctgaaat | ggtaaataaa | 540 |
| aactccgagt | taaagctgat | ttatgtgact | ccagagaaaa | ttgcaaaaag | caaaatgttt | 600 |
| atgtcaagac | tagagaaagc | ctatgaagca | aggagattta | ctcgaattgc | tgtggatgaa | 660 |
| gttcactgct | gtagtcagtg | gggacatgat | ttcagacctg | attataaggc | acttggtatc | 720 |
| ttaaagcggc | agttccctaa | cgcatcacta | attgggctga | ctgcaactgc | aacaaatcac | 780 |
| gttttgacgg | atgctcagaa | aattttgtgc | attgaaaagt | gttttacttt | tacagcttct | 840 |
| tttaataggc | caaatctata | ttatgaggtt | cggcagaagc | cctcaaacac | tgaagatttt | 900 |
| attgaggata | ttgtaaagct | cattaatggg | agatacaaag | ggcaatcagg | aatcatatat | 960 |
| tgttttctc | agaaagactc | tgaacaagtt | acggttagtt | tgcagaatct | gggaattcat | 1020 |
| gcaggtgctt | accatgccaa | tttggagcca | gaagataaga | ccacagttca | tagaaaatgg | 1080 |
| tcagccaatg | aaaattcaggt | agtagtggca | actgttgcat | ttggtatggg | aattgataag | 1140 |
| ccagatgtga | ggtttgttat | ccatcattca | atgagtaaat | ccatggaaaa | ttattaccaa | 1200 |
| gagagtggac | gtgcaggtcg | agatgacatg | aaagcagact | gtattttgta | ctacggcttt | 1260 |
| ggagatatat | tcagaataag | ttcaatggtg | gtgatggaaa | atgtgggaca | gcagaagctt | 1320 |
| tatgagatgg | tatcatactg | tcaaaacata | agcaaatgtc | gtcgtgtgtt | gatggctcaa | 1380 |
| cattttgatg | aagtatggaa | ctcagaagca | tgtaacaaaa | tgtgcgataa | ctgctgtaaa | 1440 |
| gacagtgcat | ttgaaagaaa | gaacataaca | gagtactgca | gagatctaat | caagatcctg | 1500 |
| aagcaggcag | aggaactgaa | tgaaaaactc | actccattga | aactgattga | ttcttggatg | 1560 |
| ggaaagggtg | cagcaaaact | gagagtagca | ggtgttgtgg | ctcccacact | tcctcgtgaa | 1620 |
| gatctggaga | agattattgc | acactttcta | atacagcagt | atcttaaaga | agactacagt | 1680 |
| tttacagctt | atgctaccat | ttcgtatttg | aaaataggac | taaagctaa | tcttctgaac | 1740 |
| aatgaggcac | atgctattac | tatgcaagtg | acaaagtcca | cgcagaactc | tttcagggct | 1800 |
| gaatcgtctc | aaacttgtca | ttctgaacaa | ggtgataaaa | agatggagga | aaaaaattca | 1860 |
| ggcaacttcc | agaagaaggc | tgcaaacatg | cttcagcaat | ctggttctaa | gaatacagga | 1920 |
| gctaagaaaa | gaaaaatcga | tgatgcctga | | | | 1950 |

<210> SEQ ID NO 20
<211> LENGTH: 19
<212> TYPE: DNA
<213> ORGANISM: Homo sapiens

```
<400> SEQUENCE: 20
gttcagacca cttcagctt                                                    19

<210> SEQ ID NO 21
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(16)
<223> OTHER INFORMATION: um
<220> FEATURE:
<221> NAME/KEY: modified_base
<222> LOCATION: (17)..(17)
<223> OTHER INFORMATION: cm

<400> SEQUENCE: 21
cuuacgcuga guacuucgat t                                                 21

<210> SEQ ID NO 22
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (11)..(11)
<223> OTHER INFORMATION: cm
```

```
<220> FEATURE:
<221> NAME/KEY: modified_base
<222> LOCATION: (16)..(16)
<223> OTHER INFORMATION: um

<400> SEQUENCE: 22
ucgaaguacu cagcguaagt t                                              21

<210> SEQ ID NO 23
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (13)..(13)
<223> OTHER INFORMATION: um

<400> SEQUENCE: 23
guucagacca cuucagcuut t                                              21

<210> SEQ ID NO 24
<211> LENGTH: 21
<212> TYPE: DNA
<213> ORGANISM: Artificial
<220> FEATURE:
<223> OTHER INFORMATION: Combined DNA/RNA molecule: Synthetic
      oligonucleotide
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(13)
<223> OTHER INFORMATION: um
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(19)
<223> OTHER INFORMATION: um
```

```
<400> SEQUENCE: 24
guucagacca cuucagcuut t                                            21
```